(12) United States Patent
Oomori et al.

(10) Patent No.: US 11,993,806 B2
(45) Date of Patent: May 28, 2024

(54) METHOD OF DETECTING OR METHOD OF QUANTIFYING OLIGONUCLEOTIDES

(71) Applicant: SEKISUI MEDICAL CO., LTD., Tokyo (JP)

(72) Inventors: Akane Oomori, Tokyo (JP); Koichi Shibusawa, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 420 days.

(21) Appl. No.: 17/274,813

(22) PCT Filed: Sep. 10, 2019

(86) PCT No.: PCT/JP2019/035500
§ 371 (c)(1),
(2) Date: Mar. 10, 2021

(87) PCT Pub. No.: WO2020/054700
PCT Pub. Date: Mar. 19, 2020

(65) Prior Publication Data
US 2022/0049284 A1  Feb. 17, 2022

(30) Foreign Application Priority Data

Sep. 11, 2018 (JP) .................................. 2018-169340

(51) Int. Cl.
*C12Q 1/68* (2018.01)
*C12Q 1/682* (2018.01)
(Continued)

(52) U.S. Cl.
CPC ........... *C12Q 1/682* (2013.01); *C12Q 1/6851* (2013.01); *C12Q 1/6876* (2013.01)

(58) Field of Classification Search
CPC ..... C12Q 1/682; C12Q 1/6851; C12Q 1/6876; C12Q 1/6818; C12Q 2521/307; C12Q 2565/101; C12Q 2565/50
See application file for complete search history.

(56) References Cited

U.S. PATENT DOCUMENTS 7,632,639 B2 * 12/2009 Usui ...................... C12Q 1/682
                                                     435/6.12
2006/0286553 A1  12/2006 Usui et al.
2015/0299788 A1  10/2015 Fujikawa et al.

FOREIGN PATENT DOCUMENTS

EP   2 851 425 A1    3/2015
JP   2003-116598 A   4/2003
(Continued)

OTHER PUBLICATIONS

Extended European Search Report dated Jul. 1, 2022, in European Patent Application No. 19858771.9.
(Continued)

*Primary Examiner* — Stephanie K Mummert
(74) *Attorney, Agent, or Firm* — Birch, Stewart, Kolasch & Birch, LLP

(57) ABSTRACT

The present invention provides a method of detecting and a method of quantifying oligonucleotides with more excellent specificity and quantitativity as compared to conventional signal amplification (PALSAR) measurement methods.
In the present invention, the problem is solved by hybridizing a target oligonucleotide to be measured with a complementary nucleic acid probe (3'-complementary sequence of target sequence-5'), or hybridizing the target oligonucleotide to be measured having given bases such as poly(A) added thereto with a complementary nucleic acid probe (3'-complementary sequence of target oligonucleotide+complementary sequence of given bases-5'), decomposing and removing an incomplete hybridization product by using a (Continued)

single-strand-specific nuclease such as S1 nuclease, and measuring the nucleic acid probe contained in a remaining complete hybridization product by a PALSAR method.

13 Claims, 4 Drawing Sheets

Specification includes a Sequence Listing.

(51) Int. Cl.
*C12Q 1/6851* (2018.01)
*C12Q 1/6876* (2018.01)

(56) References Cited

FOREIGN PATENT DOCUMENTS

| WO | WO 03/040367 A1 | 5/2003 |
|---|---|---|
| WO | WO 2010/087409 A1 | 8/2010 |
| WO | WO 2013/049231 A1 | 4/2013 |
| WO | WO 2013/172305 A1 | 11/2013 |
| WO | WO 2014/005038 A1 | 1/2014 |
| WO | WO 2014/153408 A1 | 9/2014 |
| WO | WO2020/054700 A1 | 10/2020 |

OTHER PUBLICATIONS

Ando et al., "In Vivo Imaging of Liposomal Small Interfering RNA (siRNA) Trafficking by Positron Emission Tomography", Yakugaku Zasshi, vol. 132, No. 12, 2012, pp. 1373-1381.
Chen et al., "Real-time quantification of microRNAs by stem-loop RT-PCR", Nucleic Acids Research, vol. 33, No. 20, e179, Nov. 27, 2005, pp. 1-9.
Healey et al., "Development of Pre-Clinical Models for Evaluating the Therapeutic Potential of Candidate siRNA Targeting STAT6", PLOS ONE, vol. 9, Issue 2, e90338, Feb. 27, 2014, pp. 1-13.
International Serch Report issued in PCT/JP2019/035500 (PCT/ISA/210), dated Jan. 28, 2020.
Wei et al., "A Specific Picomolar Hybridization-Based ELISA Assay for the Determination of Phosphorothioate Oligonucleotides in Plasma and Cellular Matrices", Pharmaceutical Research, vol. 23, No. 6, Jun. 2006, pp. 1251-1264.
Written Opinion of the International Searching Authority issued in PCT/JP2019/035500 (PCT/ISA/237), dated Jan. 28, 2020.
Yu et al., "Development of an Ultrasensitive Noncompetitive Hybridization-Ligation Enzyme-Linked Immunosorbent Assay for the Determination of Phosphorothioate Oligodeoxynucleotide in Plasma", Analytical Biochemistry, vol. 304, May 1, 2002, pp. 19-25.
International Preliminary Report on Patentability and English translation of the Written Opinion of the International Searching Authority for International Application No. PCT/JP2019/035500, dated Mar. 25, 2021.
Chinese Office Action and Search Report for Chinese Application No. 201980055748.2, dated Dec. 7, 2023, with an English translation.

\* cited by examiner

[FIG.1]
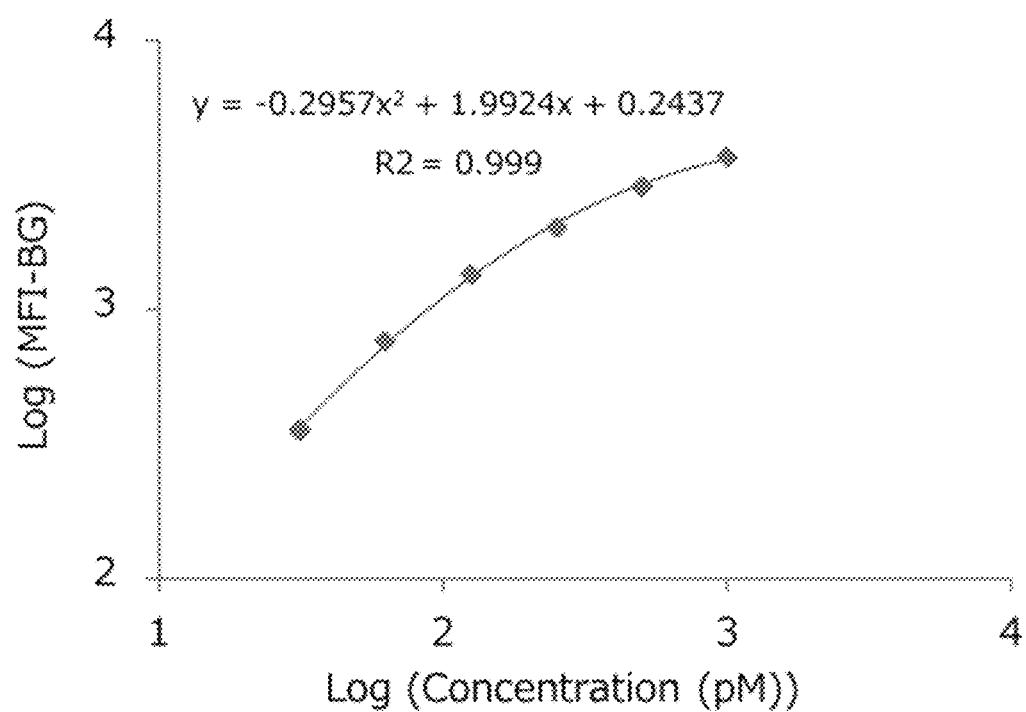

[FIG.2]
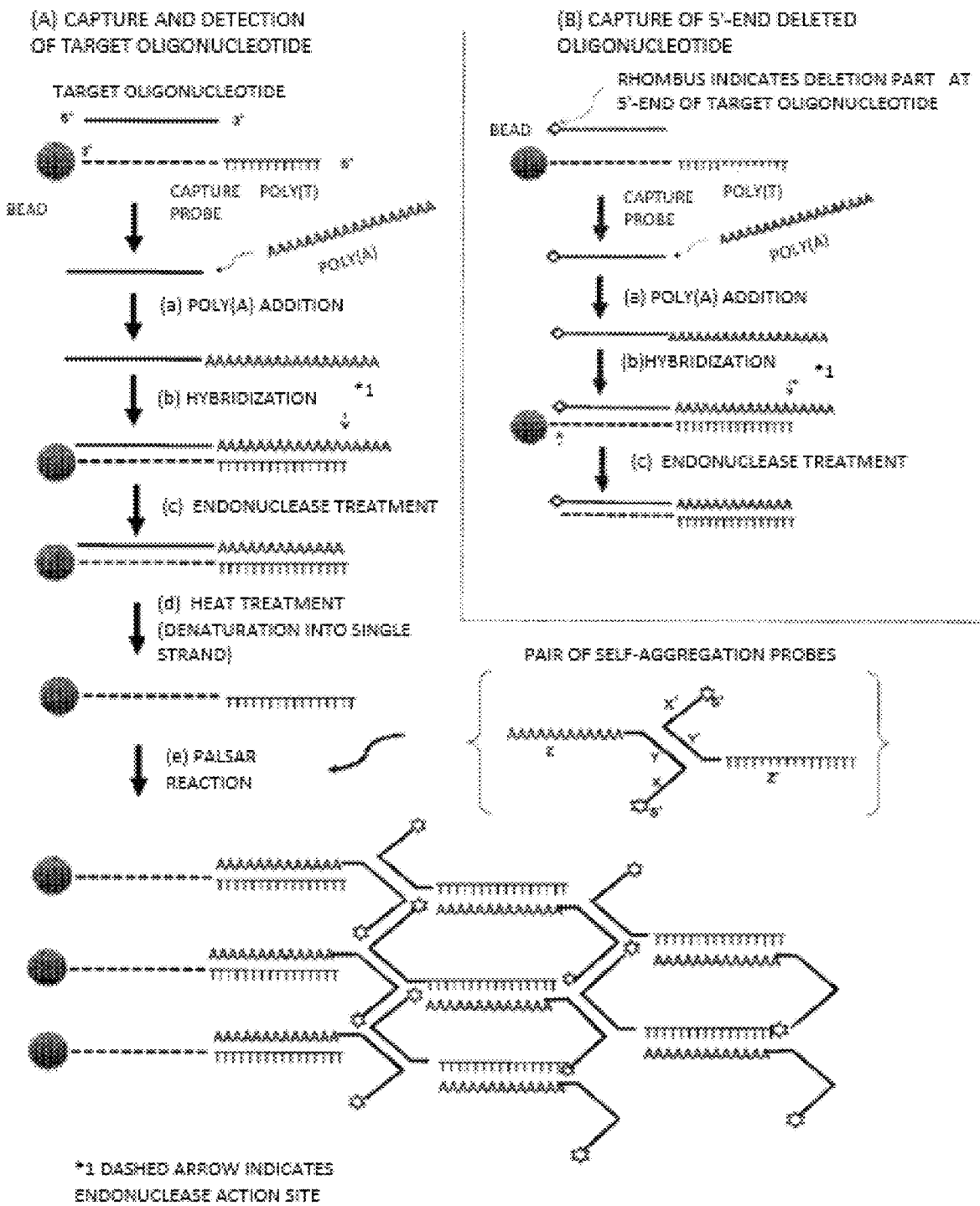

[FIG.3]
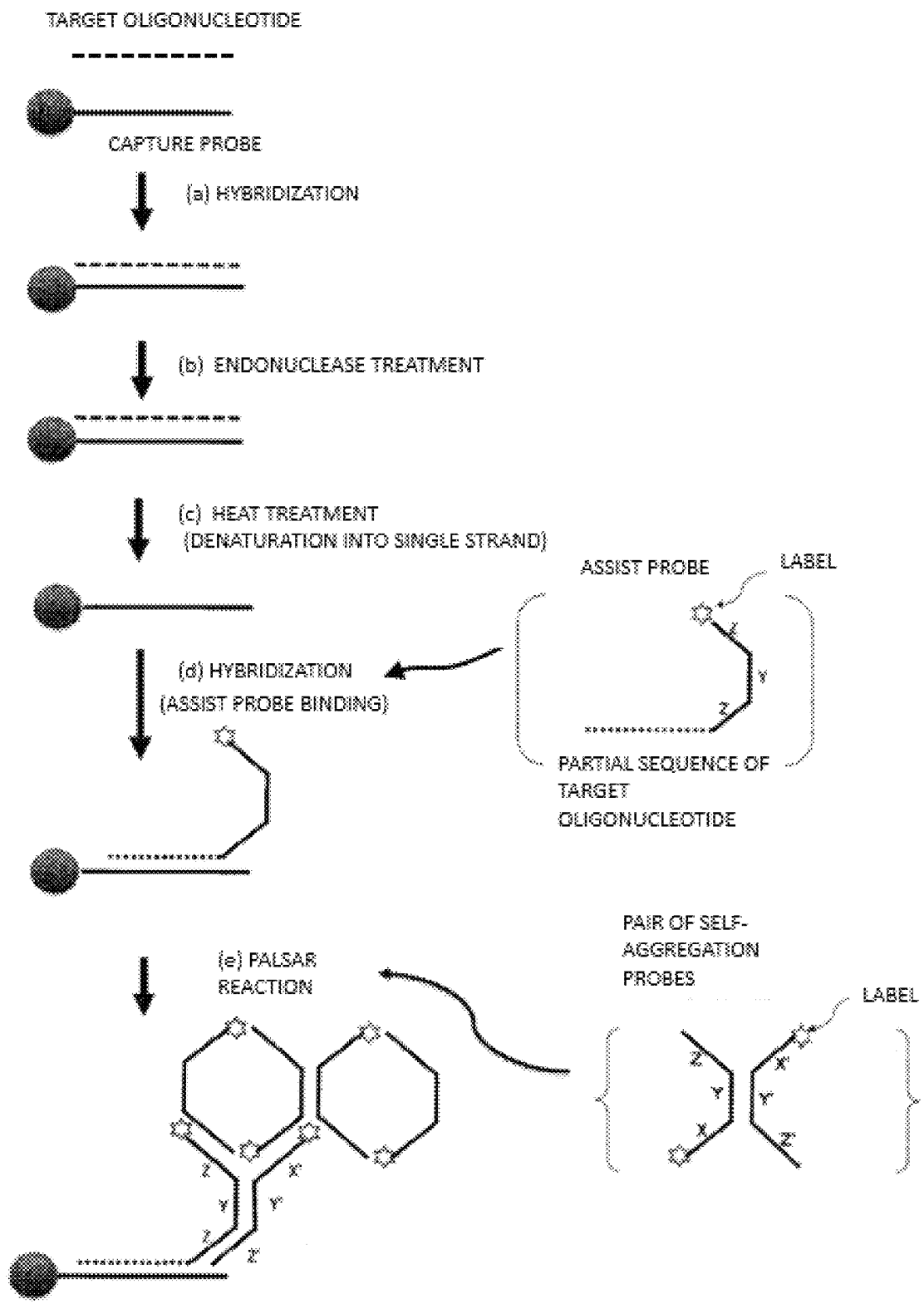

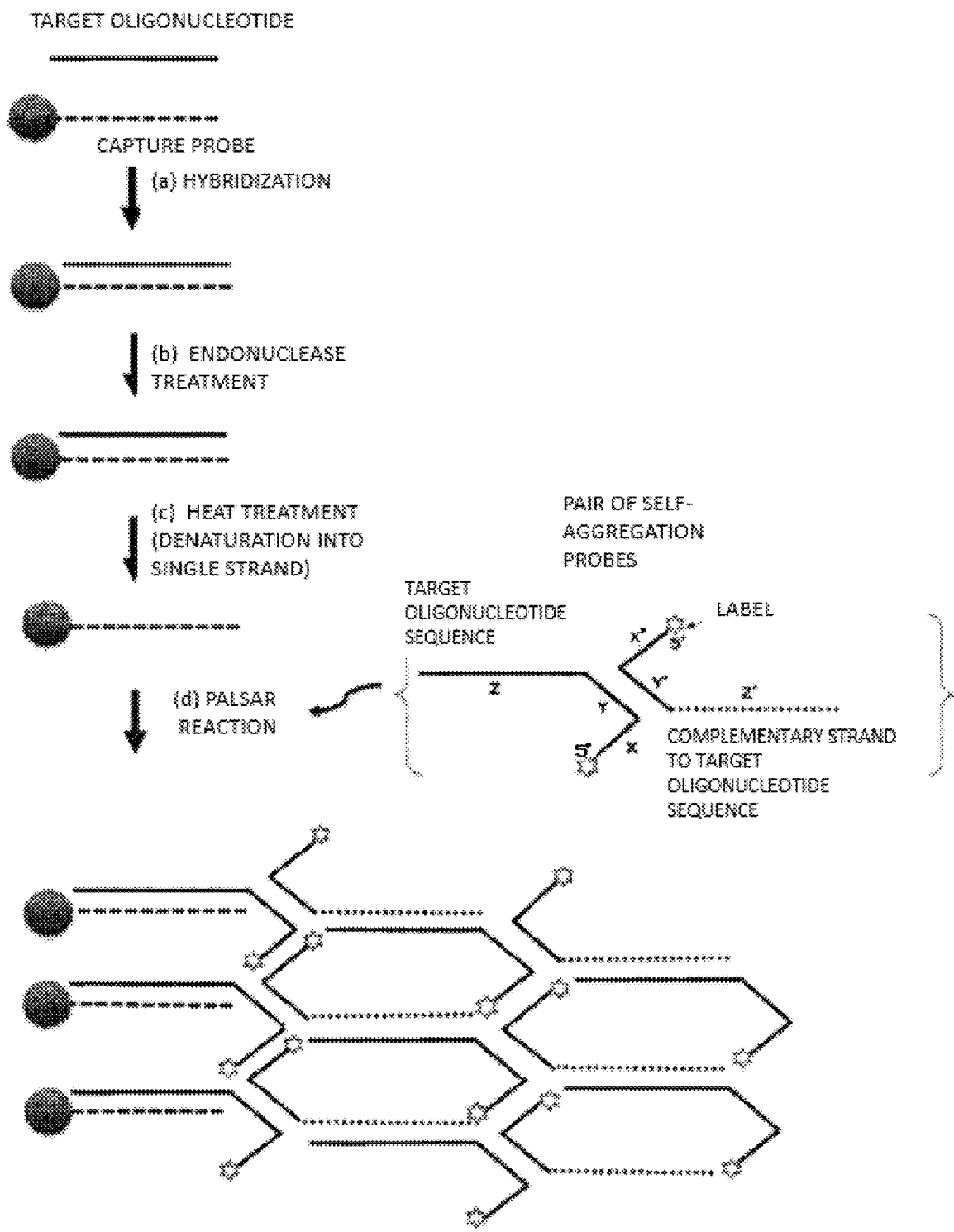
[FIG.4]

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: GTI-2040

<400> SEQUENCE: 1
ggctaaatcg ctccaccaag                                        20

<210> SEQ ID NO 2
<211> LENGTH: 19
<212> TYPE: DNA
<213> ORGANISM: Artificial Sequence
<220> FEATURE:
<223> OTHER INFORMATION: 3'N-1

<400> SEQUENCE: 2
ggctaaatcg ctccaccaa                                         19

<210> SEQ ID NO 3
<211> LENGTH: 18
<212> TYPE: DNA
<213> ORGANISM: Artificial Sequence
<220> FEATURE:
<223> OTHER INFORMATION: 3'N-2

<400> SEQUENCE: 3
ggctaaatcg ctccacca                                          18
```

```
<210> SEQ ID NO 4
<211> LENGTH: 19
<212> TYPE: DNA
<213> ORGANISM: Artificial Sequence
<220> FEATURE:
<223> OTHER INFORMATION: 5'N-1

<400> SEQUENCE: 4
gctaaatcgc tccaccaag                                                  19

<210> SEQ ID NO 5
<211> LENGTH: 20
<212> TYPE: DNA
<213> ORGANISM: Artificial Sequence
<220> FEATURE:
<223> OTHER INFORMATION: Mismatched GTI-2040

<400> SEQUENCE: 5
ggctaaactc gtccaccaag                                                 20

<210> SEQ ID NO 6
<211> LENGTH: 20
<212> TYPE: DNA
<213> ORGANISM: Artificial Sequence
<220> FEATURE:
<223> OTHER INFORMATION: Scrambled GTI-2040

<400> SEQUENCE: 6
acgcactcag ctagtgacac                                                 20

<210> SEQ ID NO 7
<211> LENGTH: 20
<212> TYPE: DNA
<213> ORGANISM: Artificial Sequence
<220> FEATURE:
<223> OTHER INFORMATION: Reverse Complementary to GTI-2040

<400> SEQUENCE: 7
cttggtggag cgatttagcc                                                 20

<210> SEQ ID NO 8
<211> LENGTH: 20
<212> TYPE: DNA
<213> ORGANISM: Artificial Sequence
<220> FEATURE:
<223> OTHER INFORMATION: poly(T)20

<400> SEQUENCE: 8
tttttttttt tttttttttt                                                 20

<210> SEQ ID NO 9
<211> LENGTH: 46
<212> TYPE: DNA
<213> ORGANISM: Artificial Sequence
<220> FEATURE:
<223> OTHER INFORMATION: Ccb4530-1-XY-20T-B

<400> SEQUENCE: 9
caacaatcag gacgataccg atgaagtttt tttttttttt tttttt                    46

<210> SEQ ID NO 10
<211> LENGTH: 46
<212> TYPE: DNA
<213> ORGANISM: Artificial Sequence
<220> FEATURE:
<223> OTHER INFORMATION: Ccb4530-2-XY-20A-B
```

```
<400> SEQUENCE: 10
gtcctgattg ttgcttcatc ggtatcaaaa aaaaaaaaaa aaaaaa                        46

<210> SEQ ID NO 11
<211> LENGTH: 47
<212> TYPE: DNA
<213> ORGANISM: Artificial Sequence
<220> FEATURE:
<223> OTHER INFORMATION: Ccb4530-2-ZYZ-8-B

<400> SEQUENCE: 11
ccaccaagca ctccttatat ccttcatcgg tatccactcc ttatatc                      47

<210> SEQ ID NO 12
<211> LENGTH: 39
<212> TYPE: DNA
<213> ORGANISM: Artificial Sequence
<220> FEATURE:
<223> OTHER INFORMATION: Ccb4530-1B

<400> SEQUENCE: 12
caacaatcag gacgataccg atgaaggata taaggagtg                               39

<210> SEQ ID NO 13
<211> LENGTH: 39
<212> TYPE: DNA
<213> ORGANISM: Artificial Sequence
<220> FEATURE:
<223> OTHER INFORMATION: Ccb4530-2B

<400> SEQUENCE: 13
gtcctgattg ttgcttcatc ggtatccact ccttatatc                               39

<210> SEQ ID NO 14
<211> LENGTH: 29
<212> TYPE: DNA
<213> ORGANISM: Artificial Sequence
<220> FEATURE:
<223> OTHER INFORMATION: Reverse Complementary to GTI-2040

<400> SEQUENCE: 14
tcgctattcc ttggtggagc gatttagcc                                          29
```

METHOD OF DETECTING OR METHOD OF QUANTIFYING OLIGONUCLEOTIDES

TECHNICAL FIELD

The present invention relates to a method of detecting and a method of quantifying oligonucleotides with high sensitivity and excellent specificity and quantitativity.

BACKGROUND ART

Nucleic acid drugs cause sequence-specific gene silencing and are therefore recently attracting significant attention as new therapeutic agents for various diseases that have been difficult to treat, such as genetic diseases and intractable diseases (Non-Patent Document 1, Ando 2012).

In pharmacokinetic/pharmacodynamic (PK/PD) screening tests at a searching stage of drug development, in safety, pharmacological, and pharmacokinetic tests at the non-clinical stage, and at the clinical stage, drug concentration is measured in animal or human biological samples having received drug administration. For receiving approval as a new drug, it is necessary to acquire data on drug concentration in biological samples and submit materials related to safety and pharmacokinetics in conformity with the guidelines established by the Ordinance of the Ministry of Health, Labor and Welfare.

Ando et al. reported that by labeling a nucleic acid drug with a positron-emitting nuclide, a behavior in a living body is three-dimensionally analyzed non-invasively and in real-time (Non-Patent Document 1, Ando 2012). Healey et al. have reported that by using a stem-loop RT-PCR method (Non-Patent Document 3, Chen 2005), a quantification lower limit of 0.01 pg/μL was achieved (Non-Patent Document 2, Healey 2014).

However, recently, the development of artificial nucleic acids and delivery materials has enabled treatment at low doses. As a result, the drug concentration in biological samples has become lower than before, and a more sensitive measurement system has been required to detect these low-concentration drugs. Furthermore, to follow the guidelines established by the Ordinance of the Ministry of Health, Labor and Welfare, the measurement system must have high quantitativity independent of an operator and therefore is not suitable for the measurement by the PCR method, which is a semiquantitative method.

Additionally, the conventional measurement system has a problem that when oligonucleotides used in nucleic acid drugs are metabolized and decomposed from the 5' or 3' end, the oligonucleotides cannot be distinguished from intact oligonucleotides to be measured, which makes it impossible to measure accurate drug concentration.

To distinguish between the intact oligonucleotides to be measured and metabolites thereof and specifically measure a nucleic acid drug having a biological activity, Yu et al. developed a hybridization-ligation ELISA method (Non-patent Document 4, Yu 2002). In this method, a "template" oligonucleotide containing a sequence complementary to the oligonucleotide to be measured and a "ligation probe" are used. The "template" oligonucleotide has an additional 9-mer nucleotide adjacent to the nucleotide having the complementary sequence at the 5' end and biotin at the 3' end. The "ligation probe" is a 9-mer oligonucleotide having a sequence complementary to the additional 9-mer nucleotide. The "ligation probe" has phosphoric acid at the 5' end and digoxigenin at the 3' end. Therefore, when the oligonucleotide to be measured is intact, the intact oligonucleotide and the ligation probe hybridize on the template oligonucleotide without a gap. By treating the product of this hybridization with ligase, the intact oligonucleotide and the ligation probe are ligated. On the other hand, if the oligonucleotide to be measured is metabolized and the nucleotide at the 3' end side is deleted, this ligation does not occur. The ligation product is bound to a solid phase by using biotin, the unreacted ligation probe is removed by washing, and digoxigenin at the 3' end of the immobilized ligation product is detected by the ELISA method (see FIG. 1 of Non-Patent Document 4, Yu 2002).

Wei et al. disclosed that S1 nuclease treatment is performed after ligase treatment so as to improve the specificity of the hybridization-ligation ELISA method (Non-Patent Document 5, Wei 2006).

However, the hybridization-ligation ELISA method is complicated and unsuitable for multiplexing since it is necessary to design an optimal ligation probe sequence in consideration of the sequence of the oligonucleotide to be measured.

To develop a highly versatile method of detecting or quantifying oligonucleotides satisfying the high requirements described above in drug development, the present inventors developed a method of detecting or quantifying oligonucleotides with high sensitivity and excellent specificity and quantitativity based on a completely new idea, thereby completing the present invention.

CITATION LIST

Patent Literature

Patent Document 1: WO 2013/172305

Non Patent Literature

Non-Patent Document 1: Ando H, Yonenaga N, Asai T, Hatanaka K, Koide H, Tsuzuku T, Harada N, Tsukada H, Oku N. [In vivo imaging of liposomal small interfering RNA (siRNA) trafficking by positron emission tomography]. Yakugaku Zasshi. 2012; 132(12):1373-81. Review.

Non-Patent Document 2: Healey G D, Lockridge J A, Zinnen S, Hopkin J M, Richards I, Walker W. Development of pre-clinical models for evaluating the therapeutic potential of candidate siRNA targeting STATE. PLoS One. 2014 Feb. 27; 9 (2): e90338.

Non-Patent Document 3: Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J. Real-time quantification of microRNAs by stem-loop RT-PCR. Nucleic Acids Res. 2005 Nov. 27; 33 (20): e179.

Non-Patent Document 4: Yu R Z, Baker B, Chappell A, Geary R S, Cheung E, Levin A A. Development of an ultrasensitive noncompetitive hybridization-ligation enzyme-linked immunosorbent assay for the determination of phosphorothioate oligodeoxynucleotide in plasma. Anal Biochem. 2002 May 1; 304(1):19-25.

Non-Patent Document 5: Wei X, Dai G, Marcucci G, Liu Z, Hoyt D, Blum W, Chan K K. A specific picomolar hybridization-based ELISA assay for the determination of phosphorothioate oligonucleotides in plasma and cellular matrices. Pharm Res. 2006 June; 23 (6):1251-64.

SUMMARY OF INVENTION

Technical Problem

The present inventor found a problem that the conventional signal amplification methods (PALSAR method, etc.) cannot distinguish an oligonucleotide in which the sequence of the target oligonucleotide to be measured is partially deleted, or particularly, an oligonucleotide deleted on the 5' side or the 3' side (such as metabolite), from the intact target oligonucleotide (unchanged form) and measure both the metabolite and the unchanged form.

A problem to be solved by the present invention is to provide a method of measuring oligonucleotides with high sensitivity and excellent specificity and quantitativity as compared to conventional methods.

Another problem to be solved by the present invention is to provide a method of measuring oligonucleotides with high sensitivity and excellent specificity and quantitativity, capable of distinguishing between the unchanged form and the metabolite and detecting only the unchanged form.

Solution to Problem

The present inventors solved the problems by hybridizing a target oligonucleotide to be measured with a complementary nucleic acid probe (3'-complementary sequence of target sequence-5'), or hybridizing the target oligonucleotide to be measured having given bases such as poly(A) (first polynucleotide) added thereto with a complementary nucleic acid probe (3'-complementary sequence of target oligonucleotide+complementary sequence of first polynucleotide-5'), decomposing and removing an incomplete hybridization product by using a single-strand-specific nuclease such as S1 nuclease, and measuring the nucleic acid probe contained in a remaining complete hybridization product.

Specifically, metabolites of the target oligonucleotide or variants of the target oligonucleotide deleted on the 5' side or 3' side form incomplete hybridization products with the nucleic acid probe and therefore are decomposed by the single-strand-specific nuclease. The decomposition products due to the single-stranded nuclease are preferably removed and, for example, can be removed by washing after immobilizing the 3' end of the nucleic acid probe on a solid phase. From the nucleic acid probe contained in the remaining complete hybridization product, the target oligonucleotide to be measured can be quantified by detecting the nucleic acid probe, or a portion of the added bases of the nucleic acid probe, by using a method (so-called PALSAR method) disclosed in this specification, which is established by improving the technique of WO 2013/172305.

Alternatively, from the nucleic acid probe contained in the remaining complete hybridization product, the target oligonucleotide to be measured can be quantified by detecting a chemical moiety such as a labeling substance added to the 5' end of the nucleic acid probe.

To detect the chemical moiety such as a labeling substance added to the 5' end of a nucleic acid probe, an ELISA method well known to those skilled in the art can be used as in Yu et al. and Wei et al.

The nucleic acid probe contained in the remaining intact hybridization product recovered in this way corresponds to an amount of the target oligonucleotide in a sample. Therefore, the present inventors also provide a method of recovering a nucleic acid probe corresponding to an amount of the target oligonucleotide having a specific sequence in a sample.

From the above, the present invention has the following configurations.

<1> A method of detecting a target oligonucleotide in a sample, comprising steps of:
(i) bringing a capture probe for capturing the target oligonucleotide into contact with the sample,
the capture probe containing
(A) a nucleic acid probe, and
(B) a solid phase, or an adapter or a linker, adjacent to a nucleotide at the 3' end or 5' end of the nucleic acid probe,
the nucleic acid probe containing a sequence complementary to a complete or partial sequence of the target oligonucleotide;
(ii) bringing a single-strand-specific nuclease into contact with the sample subjected to the contact step with the capture probe;
(iii) making the capture probe in the sample single-stranded after the contact step with the single-strand-specific nuclease is performed;
(iv) bringing a pair of probes capable of self-aggregation composed of first and second oligonucleotides into contact with the sample subjected to the step of making the capture probe single-stranded to form a complex of the capture probe and an oligonucleotide polymer generated by self-aggregation of the first and second oligonucleotides; and
(v) detecting the complex.

<2> The method of detecting a target oligonucleotide according to <1>, wherein at least one oligonucleotide of the pair of probes capable of self-aggregation composed of the first and second oligonucleotides contains the complete or partial sequence of the target oligonucleotide.

<3> The method of detecting a target oligonucleotide according to <1>, wherein
the complex forming step of (iv) includes
a step of bringing into contact with an assist probe containing both the complete or partial sequence of the target oligonucleotide and a sequence complementary to a complete or partial sequence of at least one of the first and second oligonucleotides.

<4> A method of detecting a target oligonucleotide in a sample, comprising steps of:
(i) adding a first polynucleotide to the target oligonucleotide in the sample;
(ii) bringing a capture probe for capturing the target oligonucleotide into contact with the target oligonucleotide,
the capture probe containing
(A) a nucleic acid probe,
(B) a solid phase, or an adapter or a linker, adjacent to a nucleotide at the 3' end or 5' end of the nucleic acid probe,
the nucleic acid probe containing a sequence complementary to a complete or partial sequence of the target oligonucleotide and/or a complete or partial sequence of the first polynucleotide;
(iii) bringing a single-strand-specific nuclease into contact with the sample subjected to the step of adding the first polynucleotide and the contact step with the capture probe;
(iv) making the capture probe in the sample single-stranded after the contact step with the single-strand-specific nuclease is performed;
(v) bringing a pair of probes capable of self-aggregation composed of first and second oligonucleotides into contact with the sample subjected to the step of making the capture probe single-stranded to form a complex of the capture probe and an oligonucleotide polymer generated by self-aggregation of the first and second oligonucleotides; and (vi) detecting the complex.

<5> The method of detecting a target oligonucleotide according to <4>, wherein
(i) the step of adding the first polynucleotide to the target oligonucleotide in the sample is a step of adding the first polynucleotide to the target oligonucleotide in the sample before the contact step with the capture probe.

<6> The method of detecting a target oligonucleotide according to <4>, wherein
(i) the step of adding a first polynucleotide to the target oligonucleotide in the sample is a step of adding the first polynucleotide to the target oligonucleotide in the sample after the contact step with the capture probe.

<7> The method of detecting a target oligonucleotide according to any one of <4> to <6>, wherein
at least one oligonucleotide of the pair of probes capable of self-aggregation composed of the first and second oligonucleotides contains the complete or partial sequence of the first polynucleotide.

<8> The method of detecting a target oligonucleotide according to any one of <4> to <6>, wherein
the step of forming a complex of (v) includes a step of bringing into contact with an assist probe, and wherein
the assist probe contains the complete or partial sequence of the target oligonucleotide and/or the complete or partial sequence of the first polynucleotide, and a sequence complementary to a complete or partial sequence of one of the first and second oligonucleotides.

<9> The method of detecting a target oligonucleotide according to any one of <4> to <8>, wherein the first polynucleotide has a poly(A) sequence, a poly(T) sequence, a poly(U) sequence, a poly(T/U) sequence, a poly(G) sequence, or a poly(C) sequence.

<10> The method of detecting a target oligonucleotide according to <9>, wherein the first polynucleotide has a poly(A) sequence.

<11> The method of detecting a target oligonucleotide according to any one of <1> to <10>, wherein the first oligonucleotide is an oligonucleotide containing at least a nucleic acid region X, a nucleic acid region Y, and a nucleic acid region Z in order from the 5'-end side, while the second oligonucleotide is an oligonucleotide containing at least a nucleic acid region X' complementary to the nucleic acid region X, a nucleic acid region Y' complementary to the nucleic acid region Y, and a nucleic acid region Z' complementary to the nucleic acid region Z in order from the 5'-end side.

<12> The method of detecting a target oligonucleotide according to <11>, wherein the nucleic acid region Z contains a poly(A) sequence, and wherein the nucleic acid region Z' contains a poly(T) sequence.

<13> The method of detecting a target oligonucleotide according to any one of <1> to <12>, wherein the single-strand-specific nuclease is endonuclease.

<14> A kit for detecting a target oligonucleotide in a sample, comprising:
(1) a single-strand-specific nuclease;
(2) a capture probe for capturing the target oligonucleotide; and
(3) a pair of probes capable of self-aggregation composed of first and second oligonucleotides.

<15> The kit for detecting a target oligonucleotide according to <14>, further comprising a first polynucleotide to be added to the target oligonucleotide.

<16> The kit for detecting a target oligonucleotide according to <14>, further comprising a polyadenylation enzyme adding poly(A) as the first polynucleotide to the target oligonucleotide.

<17> The kit for detecting a target oligonucleotide according to <15> or <16>, wherein
the capture probe of (2) contains
(A) a nucleic acid probe,
(B) a solid phase, or an adapter or a linker, adjacent to a nucleotide at the 3' end or 5' end of the nucleic acid probe, wherein
the nucleic acid probe contains a sequence complementary to a complete or partial sequence of the target oligonucleotide and/or a complete or partial sequence of the first polynucleotide, and wherein
in the pair of probes capable of self-aggregation of (3), at least one of the first and second oligonucleotides contains the complete or partial sequence of the first polynucleotide.

<18> The kit for detecting a target oligonucleotide according to <14>, wherein
the capture probe of (2) contains
(A) a nucleic acid probe, and
(B) a solid phase, or an adapter or a linker, adjacent to a nucleotide at the 3' end or 5' end of the nucleic acid probe, wherein
the nucleic acid probe contains a sequence complementary to the target oligonucleotide, and wherein
in the pair of probes capable of self-aggregation of (3), at least one of the first and second oligonucleotides contains the complete or partial sequence of the target oligonucleotide.

<19> The kit for detecting a target oligonucleotide according to any one of <14> to <18>, wherein the single-strand-specific nuclease of (1) is endonuclease.

<20> The kit for detecting a target oligonucleotide according to any one of <14> to <16>, further comprising an assist probe, wherein the assist probe contains the complete or partial sequence of the target oligonucleotide and/or the complete or partial sequence of the first polynucleotide, and a sequence complementary to a complete or partial sequence of one of the first and second oligonucleotides.

<21> A method of recovering a capture probe corresponding to an amount of a target oligonucleotide in a sample, comprising steps of:
(i) bringing a capture probe for capturing the target oligonucleotide into contact with the sample,
the capture probe containing
(A) a nucleic acid probe, and
(B) a solid phase, or an adapter or a linker, adjacent to a nucleotide at the 3' end or 5' end of the nucleic acid probe,
the nucleic acid probe containing a sequence complementary to a complete or partial sequence of the target oligonucleotide;
(ii) bringing a single-strand-specific nuclease into contact with the sample subjected to the contact step with the capture probe; and (iii) recovering the capture probe not cleaved by the single-strand-specific nuclease and contained in the sample after the contact step with the single-strand-specific nuclease is performed.

<22> The method of recovering a capture probe according to <21>, comprising a step of adding a first polynucleotide to the target oligonucleotide before the step of (ii) bringing a single-strand-specific nuclease into contact with the sample, wherein
the nucleic acid probe contains a sequence complementary to the complete or partial sequence of the target oligonucleotide and/or a complete or partial sequence of the first polynucleotide.

<23> The method of recovering a capture probe according to <21>, comprising a step of adding a first polynucleotide to the target oligonucleotide before the step of (i) bringing a capture probe for capturing the target oligonucleotide into contact with the sample, wherein
the nucleic acid probe contains a sequence complementary to the complete or partial sequence of the target oligonucleotide and/or a complete or partial sequence of the first polynucleotide.

<24> A method of quantifying a target oligonucleotide in a sample, comprising steps of:
(i) bringing a capture probe for capturing the target oligonucleotide into contact with the sample,
the capture probe containing
(A) a nucleic acid probe, and
(B) a solid phase, or an adapter or a linker, adjacent to a nucleotide at the 3' end or 5' end of the nucleic acid probe,
the nucleic acid probe containing a sequence complementary to the target oligonucleotide;
(ii) bringing a single-strand-specific nuclease into contact with the sample subjected to the contact step with the capture probe;
(iii) recovering the capture probe not cleaved by the single-strand-specific nuclease and contained in the sample after the contact step with the single-strand-specific nuclease is performed; and
(iv) detecting the recovered capture probe and quantifying the target oligonucleotide in the sample.

<25> The method of quantifying a target oligonucleotide according to <24>, comprising a step of adding a first polynucleotide to the target oligonucleotide before the step of (ii) bringing a single-strand-specific nuclease into contact with the sample, wherein the nucleic acid probe contains a sequence complementary to a complete or partial sequence of the target oligonucleotide and/or a complete or partial sequence of the first polynucleotide.

<26> The method of quantifying a target oligonucleotide according to <24>, comprising a step of adding a first polynucleotide to the target oligonucleotide before the step of (i) bringing a capture probe for capturing the target oligonucleotide into contact with the sample, wherein the nucleic acid probe contains a sequence complementary to a complete or partial sequence of the target oligonucleotide and/or a complete or partial sequence of the first polynucleotide.

The present invention will hereinafter more specifically be described in terms of embodiments having a step of adding poly(A) as the first polynucleotide to the target oligonucleotide before bringing the single-strand-specific nuclease with the sample among the configurations described above (first to fifteenth embodiments).

First Embodiment

A method of recovering a nucleic acid probe in proportion to an amount of a target oligonucleotide having a specific sequence in a sample, the method comprising the following steps in the order described below:
(i) a step of bringing poly(A) polymerase (polynucleotide adenylyl transferase) and adenosine triphosphate (ATP) into contact with a sample containing or suspected of containing the target oligonucleotide under active conditions of the poly(A) polymerase to polyadenylate the target oligonucleotide in the sample;
(ii) a step of optionally thermally deactivating the poly(A) polymerase by a heat treatment of the sample;
(iii) a step of bringing a capture probe for capturing the target oligonucleotide into contact with the sample, wherein the capture probe contains a nucleic acid probe specifically binding to the target oligonucleotide and a solid phase adjacent to a nucleotide at the 3' end of the nucleic acid probe or an adapter or a linker fixable to the solid phase, wherein the nucleic acid probe contains a sequence completely complementary to the entire length of the target oligonucleotide or at least a 15-mer continuous portion containing the 3' end of the target oligonucleotide, at least a 15-mer continuous poly(T/U) sequence adjacent to the 5'-end nucleotide of the complementary sequence, and optionally a chemical moiety adjacent to the 5'-end nucleotide of the poly(T/U) sequence, wherein the contact is achieved under conditions enabling all corresponding bases of the polyadenylated target oligonucleotide and the completely complementary sequence of the nucleic acid probe to form Watson-Crick base pairs;
(iv) a step of bringing a single-strand-specific endonuclease into contact with the sample subjected to the contact step with the capture probe;
(v) a step of washing the solid phase contained in the sample subjected to the contact step with the single-strand-specific endonuclease, wherein the adapter or linker is immobilized on the solid phase before the washing step; and
(vi) a step of recovering the nucleic acid probe bound to the solid phase after washing as a nucleic acid probe in proportion to the amount of the target oligonucleotide in the sample.

Second Embodiment

A method of quantifying a target oligonucleotide having a specific sequence in a sample by detecting a chemical moiety contained in a nucleic acid probe, the method comprising the following steps in the order described below:
(vii) a step of bringing poly(A) polymerase (polynucleotide adenylyl transferase) and adenosine triphosphate (ATP) into contact with a sample containing or suspected of containing the target oligonucleotide under active conditions of the poly(A) polymerase to polyadenylate the target oligonucleotide in the sample;
(viii) a step of optionally thermally deactivating the poly(A) polymerase by a heat treatment of the sample;
(ix) a step of bringing a capture probe for capturing the target oligonucleotide into contact with the sample, wherein the capture probe contains a nucleic acid probe specifically binding to the target oligonucleotide and a solid phase adjacent to a nucleotide at the 3' end of the nucleic acid probe or an adapter or a linker fixable to the solid phase, wherein the nucleic acid probe contains a sequence completely complementary to the entire length of the target oligonucleotide or at least a 15-mer continuous portion containing the 3' end of the target oligonucleotide, at least a 15-mer continuous poly(T/U) sequence adjacent to the 5'-end nucleotide of the complementary sequence, and a chemical moiety (labeling substance) adjacent to the 5'-end nucleotide of the poly(T/U) sequence, wherein the contact is achieved under conditions enabling all corresponding bases of the polyadenylated target oligonucleotide and the completely complementary sequence of the nucleic acid probe to form Watson-Crick base pairs;

(x) a step of bringing a single-strand-specific endonuclease into contact with the sample subjected to the contact step with the capture probe;

(xi) a step of washing the solid phase contained in the sample subjected to the contact step with the single-strand-specific endonuclease, wherein the adapter or linker is immobilized on the solid phase before the washing step;

(xii) a step of detecting the chemical moiety linked to the solid phase via the nucleic acid probe by detecting light emitted by the chemical moiety, or by using a labeled antibody specifically binding to the chemical moiety, to quantify the capture probe not cleaved by the single-strand-specific endonuclease; and (xiii) a step of correlating the amount of the quantified capture probe with the amount of the target oligonucleotide in the sample.

Third Embodiment

A method of quantifying a target oligonucleotide having a specific sequence in a sample by detecting a poly(T/U) sequence contained in the nucleic acid probe, the method comprising the following steps in the order described below:

(xiv) a step of bringing poly(A) polymerase (polynucleotide adenylyl transferase) and adenosine triphosphate (ATP) into contact with a sample containing or suspected of containing the target oligonucleotide under active conditions of the poly(A) polymerase to polyadenylate the target oligonucleotide in the sample;

(xv) a step of optionally thermally deactivating the poly (A) polymerase by a heat treatment of the sample;

(xvi) a step of bringing a capture probe for capturing the target oligonucleotide into contact with the sample, wherein the capture probe contains a nucleic acid probe specifically binding to the target oligonucleotide and a fine particle having a first fluorescent substance on a surface adjacent to the 3'-end nucleotide of the nucleic acid probe, wherein the nucleic acid probe contains a sequence completely complementary to the entire length of the target oligonucleotide or at least a 15-mer continuous portion containing the 3' end of the target oligonucleotide, at least a 15-mer continuous poly(T/U) sequence adjacent to the 5'-end nucleotide of the complementary sequence, and optionally a chemical moiety adjacent to the 5'-end nucleotide of the poly(T/U) sequence, wherein the contact is achieved under conditions enabling all corresponding bases of the polyadenylated target oligonucleotide and the completely complementary sequence of the nucleic acid probe to form Watson-Crick base pairs;

(xvii) a step of bringing a single-strand-specific endonuclease into contact with the sample subjected to the contact step with the capture probe;

(xviii) a step of heat-treating the sample subjected to the contact step with the single-strand-specific endonuclease, at a temperature at which the nucleic acid probe is heat-denatured, (xix) a step of bringing a pair of probes capable of self-aggregation composed of first and second oligonucleotides into contact with the sample subjected to the heat treatment step, wherein at least one of the first and second oligonucleotides is labeled with a labeling substance;

(xx) a step of precipitating a three-component complex of the capture probe and the self-aggregated first and second oligonucleotides by a centrifugation method or separating the complex by a suction filtration method;

(xxi) a step of optionally resuspending the precipitate in a wash buffer and precipitating the complex by a centrifugation method or separating the complex by a suction filtration method again;

(xxii) a step of bringing a conjugate of a second fluorescent substance and a substance specifically binding to the labeling substance into contact with the precipitate of the step (xx) or (xxi) in a buffer solution to obtain a fluorescent substance reaction solution;

(xxiii) a step of precipitating a four-component complex of the capture probe, the self-aggregated first and second oligonucleotides, and the conjugate by a centrifugation method or separating the complex by a suction filtration method;

(xxiv) a step of optionally resuspending the precipitate in a wash buffer and precipitating the complex by a centrifugation method or separating the complex by a suction filtration method again;

(xxv) a step of resuspending the precipitate of the step (xxiii) or (xxiv) in a wash buffer and detecting a first fluorescence emitted by the first fluorescent substance and a second fluorescence emitted by the second fluorescent substance by using a flow cytometry method.

Fourth Embodiment

The method according to the third embodiment, comprising, after step (xxv) according to the third embodiment,
(xxvi) a step of determining a concentration of the oligonucleotide in the sample by comparing an intensity of the second fluorescence when the first fluorescence and the second fluorescence are detected at the same time with an intensity of the second fluorescence when the first fluorescence and the second fluorescence are detected at the same time in a control sample containing the oligonucleotide at a known concentration.

Fifth Embodiment

The method according to the third or fourth embodiment, wherein the first oligonucleotide is an oligonucleotide containing at least a nucleic acid region X, a nucleic acid region Y, and a nucleic acid region Z in order from the 5'-end side, while the second oligonucleotide is an oligonucleotide containing at least a nucleic acid region X' complementary to the nucleic acid region X, a nucleic acid region Y' complementary to the nucleic acid region Y, and a nucleic acid region Z' complementary to the nucleic acid region Z in order from the 5'-end side.

Sixth Embodiment

The method according to the fifth embodiment, wherein the nucleic acid region Z contains a poly(T) sequence, and wherein the nucleic acid region Z' contains a poly(A) sequence.

Seventh Embodiment

The method according to any one of the third to sixth embodiments, wherein the first oligonucleotide is an oligonucleotide represented by SEQ ID NO: 9.

Eighth Embodiment

The method according to any one of the third to seventh embodiments, wherein the second oligonucleotide is an oligonucleotide represented by SEQ ID NO: 10.

Ninth Embodiment

The method according to the first or second embodiment, wherein the solid phase is a fine particle.

Tenth Embodiment

The method according to any one of the third to ninth embodiments, wherein the fine particle is a bead made of magnetic or non-magnetic polystyrene having a diameter of 1 to 10 μm.

Eleventh Embodiment

The method according to any one of the first to tenth embodiments, wherein when the nucleic acid probe specifically binds to the polyadenylated target oligonucleotide, the nucleic acid probe has a sequence forming a structure of a completely matched double-stranded nucleic acid, or a structure composed of a completely matched double-stranded nucleic acid portion and a 5'-protruding-end portion in one or both strands, or a structure composed of a completely matched double-stranded nucleic acid portion and a 3'-protruding-end portion in the polyadenylated target oligonucleotide strand, or a structure composed of a completely matched double-stranded nucleic acid portion and 5'-protruding-end and 3'-protruding-end portions in the polyadenylated target oligonucleotide strand.

Twelfth Embodiment

The method according to any one of the first to eleventh embodiments, wherein the sample is a body fluid (whole blood, serum, plasma, lymph, urine, saliva, tear fluid, sweat, gastric juice, pancreatic juice, bile, pleural fluid, synovial fluid, cerebrospinal fluid, spinal fluid, or bone marrow fluid) or tissue (liver, kidney, lung, or heart) of a human, a rodent (rat, mouse, or guinea pig), or a non-rodent animal (monkey, dog, or pig).

Thirteenth Embodiment

The method according to the first or second embodiment, wherein the adapter or linker fixable to the solid phase is biotin.

Fourteenth Embodiment

The method according to any one of the first to thirteenth embodiments, wherein the chemical moiety is digoxigenin.

Fifteenth Embodiment

The method according to any one of the first to fourteenth embodiments, wherein the single-strand-specific endonuclease is S1 nuclease.

Advantageous Effects of Invention

According to the present invention, oligonucleotides can be detected or quantified with high sensitivity and excellent specificity and quantitativeness.

Additionally, the present invention can provide the method of detecting or the method of quantifying oligonucleotides with excellent specificity and quantitativeness capable of distinguishing the oligonucleotide metabolite of the target oligonucleotide to be measured deleted on the 5' side or the 3' side from the unchanged form by a signal amplification method (such as a PALSAR method) so that only the unchanged form can be detected.

BRIEF DESCRIPTION OF DRAWINGS

FIG. 1 shows a result of quantification of target oligonucleotides by a method of the present invention (Example 1).

FIG. 2 is a schematic explanatory view showing steps of a method of detecting a target oligonucleotide of the present invention (Example 1, with addition of poly(A)) ((A) is the case of the target oligonucleotide, (B) is the case of the target oligonucleotide with the 5' end deleted).

FIG. 3 is a schematic explanatory view showing steps of the method of detecting a target oligonucleotide of the present invention (Example 2, without addition of a polynucleotide, with the use of an assist probe).

FIG. 4 is a schematic explanatory view showing steps of the method of detecting a target oligonucleotide of the present invention (without addition of a polynucleotide).

DESCRIPTION OF EMBODIMENTS (Target Oligonucleotide)

As used herein, the term "target oligonucleotide" refers to any oligonucleotide capable of forming a specific hybrid with a nucleic acid probe, and the oligonucleotide may be either DNA or RNA, may be either single-stranded or double-stranded, and may be chemically modified. Examples of chemical modification include phosphorothioate modification (PS-modification), 2'-F modification, 2'-O-Methyl (2'-OMe) modification, 2'-O-Methoxyethyl (2'-MOE) modification, morpholino modification, LNA modification, $BNA^{COC}$ modification, $BNA^{NC}$ modification, ENA modification, cEt BNA modification, etc.

When the target oligonucleotide described above is double-stranded, the target oligonucleotide is made single-stranded in the present invention.

(Capture Probe)

In the present invention, the "capture probe" is a probe for capturing a target oligonucleotide and includes (A) a nucleic acid probe and (B) a solid phase, or an adapter or a linker, adjacent to a nucleotide at the 3' end or 5' end of the nucleic acid probe.

(Nucleic Acid Probe)

A first form of the "nucleic acid probe" used in the present invention contains a sequence complementary to the complete or partial sequence of the target oligonucleotide. Specifically, the nucleic acid probe contains a sequence complementary to the entire length of the target oligonucleotide or to a portion containing the 3' end or 5' end of the target oligonucleotide, the sequence is contained as in (a-1) or (a-2) below.

- (a-1) When the solid phase or the adapter or linker is adjacent to the 3'-end nucleotide, the nucleic acid probe contains a sequence complementary to the target oligonucleotide in the portion containing the 3'-end nucleotide.
- (a-2) When the solid phase or the adapter or linker is adjacent to the 5'-end nucleotide, the nucleic acid probe contains a sequence complementary to the target oligonucleotide in the portion containing the 5'-end nucleotide.

In the nucleic acid probe, the sequence complementary to the portion containing the 3' end or 5' end of the target oligonucleotide preferably contains a sequence complementary to at least a 4-mer portion, more preferably contains a sequence complementary to at least a 10-mer portion, most preferably contains a sequence complementary to at least a 15-mer portion, of the target oligonucleotide.

The sequence complementary to the entire length of the target oligonucleotide only needs to have an identity enabling hybridization to the entire length and is more preferably a sequence completely complementary to the entire length.

Another form of the nucleic acid probe of the present invention will be described.

When the first polynucleotide is added to the target oligonucleotide, the nucleic acid probe contains a sequence complementary to the complete or partial sequence of the target oligonucleotide and/or the complete or partial sequence of the first polynucleotide.

Specifically, the sequence is contained as in (b-1) or (b-2) below.

- (b-1) When the solid phase or the adapter or linker is adjacent to the 3'-end nucleotide, the nucleic acid probe contains a sequence complementary to the complete or partial sequence of the target oligonucleotide and/or the complete or partial sequence of the first polynucleotide in the portion containing the 3'-end nucleotide.
- (b-2) When the solid phase or the adapter or linker is adjacent to the 5'-end nucleotide, the nucleic acid probe contains a sequence complementary to the complete or partial sequence of the target oligonucleotide and/or the complete or partial sequence of the first polynucleotide in the portion containing the 5'-end nucleotide.

The bases of the first polynucleotide added to the 3' end of the target oligonucleotide preferably have a base sequence not contained in the sample to be measured so as to suppress non-specific reaction.

When a polybase (A, T/U, G, or C) is added as the first polynucleotide to the 3' end of the target oligonucleotide, the nucleic acid probe contains a polybase (T/U, A, C, or G) adjacent to the 5'-end nucleotide of the sequence complementary to the target oligonucleotide.

When poly(A) is added to the 3' end of the target oligonucleotide, the nucleic acid probe contains a poly(T/U) adjacent to the 5'-end nucleotide of the sequence complementary to the target oligonucleotide.

When the nucleic acid probe specifically binds to the polyadenylated (synonymous with poly(A)-added) target oligonucleotide, the nucleic acid probe desirably has a sequence forming a structure of a completely matched double-stranded nucleic acid, or a structure composed of a completely matched double-stranded nucleic acid portion and a 5'-protruding-end portion in one or both strands, or a structure composed of a completely matched double-stranded nucleic acid portion and a 3'-protruding-end portion in the polyadenylated target oligonucleotide strand, or a structure composed of a completely matched double-stranded nucleic acid portion and 5'-protruding-end and 3'-protruding-end portions in the polyadenylated target oligonucleotide strand.

The length (number of bases) of the complementary sequence is preferably at least 4-mer bases, more preferably at least 10-mer bases, and further preferably at least 15-mer bases. At least 4-mer means 4-mer or more, 10-mer or more, 15-mer or more, 20-mer or more, 25-mer or more, 30-mer or more, 35-mer or more, 40-mer or more, 45-mer or more, or 50-mer or more, preferably 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer. The upper limit of the length of the complementary sequence is preferably 100-mer or less.

The "nucleic acid probe" used in the present invention preferably contains the sequence complementary to the target oligonucleotide in at least a continuous 4-mer portion, at least a continuous 10-mer portion, at least a continuous 15-mer portion, at least a continuous 16-mer portion, at least a continuous 17-mer portion, at least a continuous 18-mer portion, at least a continuous 19-mer portion, at least a continuous 20-mer portion, at least a continuous 21-mer portion, at least a continuous 22-mer portion, at least a continuous 23-mer portion, at least a continuous 24-mer portion, at least a continuous 25-mer portion, at least a continuous 26-mer portion, at least a continuous 27-mer portion, at least a continuous 28-mer portion, at least a continuous 29-mer portion, at least a continuous 30-mer portion, at least a continuous 31-mer portion, at least a continuous 32-mer portion, at least a continuous 33-mer portion, at least a continuous 34-mer portion, at least a continuous 35-mer portion, at least a continuous 36-mer portion, at least a continuous 37-mer portion, at least a continuous 38-mer portion, at least a continuous 39-mer portion, at least a continuous 40-mer portion, at least a continuous 41-mer portion, at least a continuous 42-mer portion, at least a continuous 43-mer portion, at least a continuous 44-mer portion, at least a continuous 45-mer portion, at least a continuous 46-mer portion, at least a continuous 47-mer portion, at least a continuous 48-mer portion, at least a continuous 49-mer portion, or at least a continuous 50-mer portion, preferably contains the sequence complementary to the target oligonucleotide in at least a continuous 15-mer portion, at least a continuous 16-mer portion, at least a continuous 17-mer portion, at least a continuous 18-mer portion, at least a continuous 19-mer portion, at least a continuous 20-mer portion, at least a continuous 21-mer portion, at least a continuous 22-mer portion, at least a continuous 23-mer portion, at least a continuous 24-mer portion, at least a continuous 25-mer portion, at least a continuous 26-mer portion, at least a continuous 27-mer portion, at least a continuous 28-mer portion, at least a continuous 29-mer portion, or at least a continuous 30-mer portion, and more preferably contains the sequence complementary to the target oligonucleotide in at least a continuous 18-mer portion, at least a continuous 19-mer portion, at least a continuous 20-mer portion, at least a continuous 21-mer portion, or at least a continuous 22-mer portion.

(Solid Phase)

As used herein, the term "solid phase" refers to insoluble fine particles, microbeads, fluorescent fine particles, magnetic particles, microtiter plates, microarrays, glass slides, substrates such as electrically conductive substrates, etc., and the solid phase is preferably fluorescent particles, more preferably fluorescent beads, and particularly preferably beads having a fluorescent substance on surfaces. The "beads having a fluorescent substance on surfaces" used in the present invention are not particularly limited as long as the beads have a fluorescent substance, and for example, MicroPlex™ Microspheres of Luminex can suitably be used. One or more types of beads can be used. By using multiple types of color-coded beads, the method of quantifying oligonucleotides of the present invention can easily be multiplexed.

The solid phase and the nucleic acid probe may directly be bound or may be bound via an adapter or a linker and are preferably bound via an adapter or a linker. A labeling substance may be bound to the nucleic acid probe of the present invention.

In the present invention, the term "adjacent" in "solid phase adjacent to the 3'-end or 5'-end nucleotide of the nucleic acid probe" means direct binding to the nucleotide, or binding via an adapter, a linker, etc. and the meaning of the binding will be described later.

(Adapter or Linker)

Examples of the "adapter or linker" used in the present invention include compounds having an amino group or a carboxyl group such as biotin, Spacer 9, Spacer 12, Spacer 18, Spacer C3 and other spacers, preferably 5'-Amino-Modifier C12 (12-(4-Monomethoxytritylamino)dodecyl-1-[(2-cyanoethyl)-(N,N-diisopropyl)]-phosphoramidite), biotin, etc.

For example, in a form in which a bead has a carboxyl group on a surface and the nucleic acid probe having a compound of an amino group added thereto binds to the carboxyl group on the bead surface via the amino group, the compound having an amino group is an example of a linker.

(Labeling Substance)

Suitable examples of the labeling substance in the present invention include radioactive isotopes, biotin, digoxigenin, fluorescent substances, luminescent substances, or dyes.

Specifically, by preliminarily adding radioisotopes such as $^{125}I$ and $^{32}P$, digoxigenin, luminescent/coloring substances such as acridinium ester, alkaline phosphatase for utilizing luminescent substances such as dioxetane and fluorescent substances such as 4-methylumbelliferyl phosphate, substances such as biotin for utilizing fluorescent/luminescent/coloring substances bound to avidin, or a donor fluorescent dye and an acceptor fluorescent dye for utilizing fluorescence resonance energy transfer (FRET), the target oligonucleotide can be detected.

(Binding of Nucleic Acid Probe to Solid Phase)

Examples of a method of binding the nucleic acid probe to the solid phase include a method using chemical bonding, a method using biological interaction, a method using physical adsorption, etc. In the method using chemical bonding, for example, when a carrier coated with a carboxyl group is used, a coupling reaction can be performed with an amino group labeling the oligonucleotide. The method using biological interaction can utilize a binding force between streptavidin coating a carrier and biotin modifying the nucleic acid probe, for example. In the method using physical adsorption, for example, when the solid phase having a negative charge is used, the oligonucleotide labeled with a substance having a positive charge such as an amino group can electrostatically be adsorbed to a carrier.

(First Polynucleotide Addition Reaction)

A first polynucleotide addition reaction of the present invention is a reaction of adding a polynucleotide to the 3'-end or 5' end of the target oligonucleotide and may be performed by a method in which a polynucleotide prepared in advance by nucleic acid synthesis is bound to the 3'-end or 5' end of the target oligonucleotide by an enzyme such as ligase, or a method in which nucleotides (bases) are added by an enzyme such as poly(A) polymerase.

Examples of the enzyme such as ligase include RNA ligase, T4 RNA ligase, DNA ligase, etc. When a polybase is added to the 5' end, the 5' end can be phosphorylated in advance to allow ligase to act thereon.

A lower limit of the length of the sequence of the first polynucleotide is preferably 4-mer or more, more preferably 10-mer or more, further preferably 15-mer or more. An upper limit of the length is preferably 100-mer or less. A preferable range of the length is 15-mer or more and 100-mer or less.

The sequence of the first polynucleotide is preferably a sequence not contained in the sample to be measured, and such a sequence can suppress non-specific reaction at the time of detection of the target oligonucleotide.

When the addition reaction of the first polynucleotide is an addition reaction of poly(A), this is a reaction of adding poly(A) to the 3' end or 5' end of the target oligonucleotide and may be performed by a method in which poly(A) prepared in advance by nucleic acid synthesis is bound to the 3' end or 5' end of the target oligonucleotide by ligase, or a method in which an adenyl residue is added to the 3' end of the target oligonucleotide by poly(A) polymerase (polynucleotide adenylyl transferase).

The poly(A) polymerase means a protein having an enzymatic activity for introducing an adenine residue to the 3' end of single-stranded RNA. More specifically, poly(A) polymerase derived from *Escherichia coli* is preferably used.

The target oligonucleotide can be polyadenylated by bringing poly(A) polymerase and adenosine triphosphate (ATP) into contact under active conditions of poly(A) polymerase, and in this description, poly(A) addition and poly adenylation of the target oligonucleotide are synonymously used.

A lower limit of the length of the poly(A) is preferably 4-mer or more, more preferably 10-mer or more, further preferably 15-mer or more. An upper limit of the length is 100-mer or less. A preferable range of the length is 15-mer or more and 100-mer or less.

When the polybase addition reaction is a poly(T) addition reaction, this is a reaction of adding poly(T) to the 3' end or 5' end of the target oligonucleotide and may be performed by a method in which poly(T) prepared in advance by nucleic acid synthesis is bound to the 3' end or 5' end of the target oligonucleotide by ligase etc.

Examples of the ligase etc. include RNA ligase, DNA ligase, etc.

A lower limit of the length of the poly(T) is preferably 4-mer or more, more preferably 10-mer or more, and further preferably 15-mer or more. An upper limit of the length is preferably 100-mer or less. A preferable range of the length is 15-mer or more and 100-mer or less.

Since the sequence of poly(T) is a sequence not contained in the sample to be measured, such a sequence suppresses a non-specific reaction at the time of detection of the target oligonucleotide.

The addition of poly(C) and the addition of poly(G) are performed in the same way.

The RNA ligase, the DNA ligase, and the poly(A) polymerase are preferably inactivated by heat etc. after the addition reaction.

The first polynucleotide addition reaction may be performed before a contact step with the single-strand-specific nuclease and can be performed before or after bringing the capture probe for capturing the target oligonucleotide into contact with the sample.

When the first polynucleotide is added to the target oligonucleotide before bringing the capture probe into contact with the sample, the first polynucleotide is added to the sample to form an adduct of the target oligonucleotide and the first polynucleotide (hereinafter also simply referred to as the target oligonucleotide-first polynucleotide), and the adduct and the capture probe are then hybridized so as to form a double strand of the target oligonucleotide-first polynucleotide and the capture probe.

When the first polynucleotide is added to the target oligonucleotide after bringing the capture probe into contact with the sample, the first polynucleotide is added to the target oligonucleotide after the hybridization of the target oligonucleotide with the capture probe through the contact between the sample and the capture probe, so as to form a double strand of the target oligonucleotide-first polynucleotide and the capture probe.

(Single-Strand-Specific Nuclease)

The single-strand-specific nuclease used in the present invention refers to a single-strand-specific endonuclease or a single-strand-specific exonuclease.

The "single-strand-specific endonuclease" is not particularly limited as long as it is an enzyme cleaving a nucleic acid inside a single-stranded nucleic acid sequence, examples thereof include S1 nuclease, Mung Bean nuclease, etc., and S1 nuclease is preferable. When the target oligonucleotide and the nucleic acid probe are RNAs, examples of the "single-strand-specific endonuclease" used in the present invention include RNase ONE™ Ribonuclease (Promega, catalog number: M4261) specifically decomposing single-stranded RNA (ssRNA).

The "single-strand-specific exonuclease" is not particularly limited as long as it is an enzyme cleaving single-stranded DNA or RNA from the 5' end or the 3' end, and examples thereof include exonuclease I etc.

(Step of Making Capture Probe Single-Stranded)

In this specification, a "step of making the capture probe single-stranded" is to form a single-stranded capture probe from the double strand of the hybridized target oligonucleotide and the capture probe or the double strand of the adduct of the target oligonucleotide and the first polynucleotide and the capture probe.

A method of forming the single-stranded capture probe may be any method of forming a single strand from a double strand, and the method may be heat treatment, alkali treatment, chaotrope treatment, etc., preferably heat treatment. Examples of the heat treatment include a method in which the treatment is performed at 95° C. for 3 minutes and at 50° C. for 3 minutes.

(Contact)

As used herein, the term "brought into contact" or "contact step" means placing a substance and another substance close to each other so that a chemical bond such as a covalent bond, an ionic bond, a metal bond, or a non-covalent bond is formed between these substances. In an aspect of the present invention, when a substance is "brought into contact" with another substance, this means mixing a solution containing a substance with a solution containing another substance. For example, a step of bringing ligase into contact with the sample is performed by keeping the temperature at 4 to 80° C. for 0.1 to 30 hours, preferably at 15 to 30° C. for 1 to 24 hours. A step of bringing poly(A) polymerase and ATP into contact with the sample is performed by keeping the temperature at 30 to 42° C. for 5 to 60 minutes, preferably at 37° C. for 15 minutes. A contact step between the sample and the capture probe is performed by keeping the temperature at 30 to 70° C. for 0.2 to 30 hours, or at 35 to 65° C. for 8 to 24 hours, preferably at 50° C. for 13.5 hours. A contact step between the sample and the single-strand-specific endonuclease is performed by keeping the temperature at 30 to 42° C. for 0.2 to 3 hours, or at 33 to 40° C. for 0.3 to 2 hours, preferably at 37° C. for 0.5 hours. A contact step between the sample and the first and second oligonucleotides is performed by keeping the temperature at 28 to 70° C. for 0.2 to 3 hours, or at 30 to 45° C. for 0.5 to 2 hours, preferably 30° C. for 1 hour.

The contact between the target oligonucleotide and the capture probe means that this is performed under the condition allowing hybridization of corresponding bases of complementary sequences of the target oligonucleotide and the nucleic acid probe. Similarly, the contact between a pair of probes capable of self-aggregation and a capture probe after a single-stranded step, the contact between the capture probe and an assist probe, or the contact between a pair of probes capable of self-aggregation means that this is performed under the condition allowing hybridization of corresponding bases.

(Self-Aggregation)

As used herein, the term "self-aggregation" refers to a state in which a plurality of first oligonucleotides forms a complex due to hybridization with second oligonucleotides and a state in which a plurality of the second oligonucleotides forms a complex due to hybridization with the first oligonucleotides.

(Pair of Probes Capable of Self-Aggregation)

The pair of probes "capable of self-aggregation" used in the method of the present invention refers to oligonucleotides having complementary base sequence regions making the first and second oligonucleotides hybridizable with each other so that a probe polymer can be formed through a self-aggregation reaction. Preferably, at least one of the first and second oligonucleotides is labeled with a labeling substance. In this case, "hybridizable" means that the complementary base sequence regions are completely complementary in an aspect and that the complementary base sequence regions are complementary except one or two mismatches in another aspect.

The pair of probes capable of self-aggregation can be labeled with a labeling substance in advance for detection. Suitable examples of such a labeling substance include radioactive isotopes, biotin, digoxigenin, fluorescent substances, luminescent substances, or dyes. Specifically, by preliminarily adding radioisotopes such as $^{125}$I and $^{32}$P, digoxigenin, luminescent/coloring substances such as acridinium ester, alkaline phosphatase for utilizing luminescent substances such as dioxetane and fluorescent substances such as 4-methylumbelliferyl phosphate, substances such as biotin for utilizing fluorescent/luminescent/coloring substances bound to avidin, or a donor fluorescent dye and an acceptor fluorescent dye for utilizing fluorescence resonance energy transfer (FRET), the target oligonucleotide can be detected.

Preferably, the labeling substance is biotin, and the labeling of the oligonucleotide is preferably performed by biotinylating the 5' end or the 3' end. When the labeling substance is biotin, the substance specifically binding to the labeling substance is streptavidin or avidin.

More specifically describing the pair of probes "capable of self-aggregation", the first oligonucleotide is an oligonucleotide containing at least a nucleic acid region X, a nucleic acid region Y, and a nucleic acid region Z in order from the 5'-end side, and the second oligonucleotide is an oligonucleotide containing at least a nucleic acid region X' complementary to the nucleic acid region X, a nucleic acid region Y' complementary to the nucleic acid region Y, and a nucleic acid region Z' complementary to the nucleic acid region Z in order from the 5'-end side.

When the first polynucleotide is poly(A), the nucleic acid region Z contains a poly(A) sequence and the nucleic acid region Z' contains a poly(T) sequence in an exemplified form.

At a step of bringing the pair of probes capable of self-aggregation composed of the first and second oligonucleotides into contact with the sample subjected to the step of making the capture probe single-stranded in the present invention and thereby forming a complex of the capture probe and an oligonucleotide polymer composed of the first and second oligonucleotides, the complex may be formed without an assist probe or may be formed via an assist probe.

The assist probe is a probe having a role of assisting formation of a complex of the capture probe made single-stranded by the single-strand step and the oligonucleotide polymer. A first form of the assist probe is a probe containing a sequence complementary to the complete or partial sequence of at least one of the first and second oligonucleotides and the complete or partial sequence of the target oligonucleotide.

For example, when one of the pair of probes capable of self-aggregation is XYZ, examples include (target oligonucleotide)-X'Y'X', (target oligonucleotide)-Z'Y'Z', (target oligonucleotide)-X'Y'Z', etc.

The assist probe may or may not be labeled with a labeling substance.

In another form, when the first polynucleotide is added to the target oligonucleotide, the assist probe is a probe containing a sequence complementary to the complete or partial sequence of at least one of the first and second oligonucleotides and the complete or partial sequence of the first polynucleotide.

For example, when the first polynucleotide is added and the sequence of one of the pair of probes capable of self-aggregation is XYZ, examples include (added bases)-X'Y'X', (added bases)-Z'Y'Z', target oligonucleotide (if added, added bases)-X'Y'Z', etc.

Description will hereinafter be made for each case of respective combinations of the presence/absence of addition of the first polynucleotide to the target oligonucleotide and the presence/absence of the assist probe.

The case of forming the complex of the pair of probes capable of self-aggregation and the single-stranded capture probe without the assist probe will be described.

In a first form, at least one of the first and second oligonucleotides may contain the complete or partial sequence of the target oligonucleotide.

Another form is a form used when the first polynucleotide is added to the target oligonucleotide, and at least one of the first and second oligonucleotides may contain the complete or partial sequence of the first polynucleotide.

When the complex is formed via the assist probe, the first or second oligonucleotides may be oligonucleotides capable of forming a probe polymer through a self-aggregation reaction. In this case, the assist probe may contain both the complete or partial sequence of the target oligonucleotide and the sequence complementary to the complete or partial sequence of at least one of the first and second oligonucleotides.

Another form is a form used when the first polynucleotide is added to the target oligonucleotide, and in this case, the assist probe may contain the complete or partial sequence of the target oligonucleotide and/or the complete or partial sequence of the first polynucleotide, and the sequence complementary to the complete or partial sequence of at least one of the first and second oligonucleotides.

At least one of the first and second oligonucleotides is preferably labeled with a labeling substance.

A first embodiment of a method of detecting a target oligonucleotide of the present invention will hereinafter be described as a method of detection performed by adding poly(A) as the first polynucleotide to the target oligonucleotide with reference to FIG. 2(A).

First, a sample possibly containing the target oligonucleotide and the capture probe for capturing the target oligonucleotide are prepared.

The capture probe of the present invention contains
(A) a nucleic acid probe, and
(B) beads immobilized on a nucleotide portion at the 3' end of the nucleic acid probe.

The nucleic acid probe contains the complete sequence of the target oligonucleotide and a sequence (poly(T)) complementary to the portion of the first polynucleotide (in this case, poly(A)).

Poly(A) polymerase is then allowed to act on the 3' end of the target oligonucleotide in the sample to add poly(A) (FIG. 2(A)a). Subsequently, the capture probe is brought into contact with the target oligonucleotide to which poly(A) is added. This causes hybridization between the target oligonucleotide having poly(A) added thereto and the nucleic acid probe in the capture probe, and a double strand is formed (FIG. 2(A)b).

Endonuclease, i.e., the single-strand-specific nuclease, is brought into contact. As a result, the single-stranded portion is decomposed (FIG. 2(A)c). A dashed arrow indicates a site on which endonuclease acts.

If a substance similar to the target oligonucleotide (metabolite of the target oligonucleotide deleted on the 5' side or the 3' side or a variant of the target oligonucleotide) is present in the sample, the substance forms an incomplete hybridization product with the nucleic acid probe of the present invention. The action of the target oligonucleotide deleted on the 5' side will be described with reference to FIG. 2(B). A white rhombus at the 5' end of the target oligonucleotide indicates a deletion site. Poly(A) is added to the oligonucleotide (FIG. 2(B)a), hybridization with the nucleic acid probe is performed (FIG. 2(B)b), and an endonuclease treatment is performed (FIG. 2(B)c). The endonuclease acts on the position indicated by the dashed arrow and causes decomposition at the site.

The complete double-stranded hybridization product formed by the capture probe and the target oligonucleotide and remaining undecomposed in the sample is made single-stranded (FIG. 2(A)d). Denaturation into a single strand is performed by heat treatment etc. The decomposition product generated by the endonuclease is not immobilized on the beads and therefore can be removed by washing and recovering the beads.

The nucleic acid probe contained in the remaining complete hybridization product can be quantified by the following PALSAR method.

The sample subjected to the step of making the capture probe single-stranded is brought into contact with a pair of probes capable of self-aggregation composed of first and second oligonucleotides to form a complex of the capture probe and an oligonucleotide polymer generated by self-aggregation of the first and second oligonucleotides (so-called PALSAR reaction).

In the pair of probes capable of self-aggregation composed of the first and second oligonucleotides, the first oligonucleotide is an oligonucleotide containing the nucleic acid region X, the nucleic acid region Y, and the nucleic acid region Z in order from the 5' end side, and the second oligonucleotide contains the nucleic acid region X' complementary to the nucleic acid region X, the nucleic acid region Y' complementary to the nucleic acid region Y, and the nucleic acid region Z' complementary to the nucleic acid region Z in order from the 5'-end side (hereinafter, the nucleic acid region may simply be referred to as X, Y, Z, X', Y', Z'). In this embodiment, since the first polynucleotide is poly(A), Z contains the poly(A) sequence and Z' contains the poly(T) sequence. A labeling substance is attached to the 5' ends of the first and second oligonucleotides.

Z' (poly(T)) of the single-stranded capture probe is hybridized with Z (poly(A)) of the first oligonucleotide, and X and Y of the first oligonucleotide are respectively hybridized with X' and Y' of the second oligonucleotide. X and X', Y and Y', and Z (poly(A)) and Z' (poly(T)) are repeatedly hybridized one after another to form an oligonucleotide polymer of the self-aggregation probes (FIG. 2(A)e).

The complex of the capture probe and the self-aggregated first and second oligonucleotides is separated through precipitation by a centrifugation method etc., and the labeling substance etc. of the first and second oligonucleotides can be detected to measure the concentration etc. of the target oligonucleotide.

The target oligonucleotide can also be detected by detecting the complete double-stranded hybridization product formed by the capture probe and the target oligonucleotide before the single-stranded step by heat treatment and the subsequent PALSAR reaction. For example, the target oligonucleotide can be detected by detecting the labeling substance of the capture probe having the labeling substance added to the 5' end in advance.

The target oligonucleotide can also be detected by detecting the labeling substance of the first polynucleotide having the labeling substance added to the 3' end in advance.

A second embodiment of the method of detecting a target oligonucleotide of the present invention will hereinafter be described as a method of detection performed without adding the first polynucleotide to the target oligonucleotide and via the assist probe in the self-aggregation reaction with reference to FIG. 3.

First, a sample possibly containing the target oligonucleotide and a capture probe for capturing the target oligonucleotide are prepared. Since the first polynucleotide is not added in this embodiment, the probe for capturing the target oligonucleotide contains (A) a nucleic acid probe, and
(B) beads immobilized on a nucleotide portion at the 3' end of the nucleic acid probe.

The nucleic acid probe contains a sequence complementary to the complete sequence of the target oligonucleotide.

Differences from the step of the first embodiment are that the step of adding the first polynucleotide of (FIG. 2(A)a) is not included and that a step of hybridizing the assist probe with the sample subjected to the step of making the capture probe single-stranded (FIG. 3d) is added.

The assist probe contains a partial sequence of the target oligonucleotide and sequences Z, Y, Z complementary to the second oligonucleotide, and the 3' end is labeled with a labeling substance.

In the pair of probes capable of self-aggregation composed of the first and second oligonucleotides, the first oligonucleotide is an oligonucleotide containing X, Y, and Z in order from the 5'-end side, and the second oligonucleotide contains X', Y', and Z' in order from the 5'-end side.

When the assist probe is brought into contact with the sample subjected to the step of making the capture probe single-stranded, hybridization occurs between the sequence complementary to the target oligonucleotide contained in the capture probe and the sequence of the target oligonucleotide of the assist probe (FIG. 3d). When the pair of probes capable of self-aggregation are brought into contact therewith, Y and Z of the assist probe hybridize with Y' and Z' of the second oligonucleotide, and X and X', Y and Y', and Z and Z' are repeatedly hybridized one after another to form an oligonucleotide polymer of the self-aggregation probes (FIG. 3e). The complex of the capture probe, the assist probe, and the self-aggregated first and second oligonucleotides is separated, and the labeling substance etc. of the first and second oligonucleotides can be detected to measure the concentration etc. of the target oligonucleotide. The target oligonucleotide can also be detected by detecting the complete double-stranded hybridization product associated with the beads before performing the PALSAR reaction. For example, the target oligonucleotide can be detected by detecting the labeling substance of the assist probe having the labeling substance added to the 3' end in advance.

A third embodiment of the method of detecting a target oligonucleotide of the present invention will hereinafter be described as a method of detection performed without adding the first polynucleotide to the target oligonucleotide and without the assist probe in the self-aggregation reaction with reference to FIG. 4.

The difference from the second embodiment is that the step of bringing the capture probe into contact with the assist probe (FIG. 3d) is not included. In the pair of probes capable of self-aggregation composed of the first and second oligonucleotides, the first oligonucleotide is an oligonucleotide containing X, Y, and Z in order from the 5'-end side, and the second oligonucleotide contains X', Y', and Z' in order from the 5'-end side.

In this case, Z is the complete sequence of the target oligonucleotide and is the sequence not hybridizing with the completely complementary sequence of the substance similar to the target oligonucleotide, and Z' is the sequence complementary to Z.

A sequence portion complementary to the target oligonucleotide, i.e., the nucleic acid probe of the single-stranded capture probe, hybridizes with the complete sequence of the target oligonucleotide, which is the Z region of the first oligonucleotide. X and X', Y and Y', Z (target oligonucleotide) and Z' (complementary strand to the target oligonucleotide) are repeatedly hybridized one after another to form an oligonucleotide polymer of the self-aggregation probes (FIG. 4d). The complex of the capture probe and the self-aggregated first and second oligonucleotides is separated, and the labeling substance etc. of the first and second oligonucleotides can be detected to measure the concentration etc. of the target oligonucleotide.

A method utilizing self-aggregation for quantifying the single-stranded capture probe complementary to the target oligonucleotide is a method known as the so-called PAL-SAR method.

Specific examples of the PALSAR method are shown in FIGS. 4 to 14 of WO 2013/172305 etc. and can appropriately be modified and applied to the self-aggregation reaction of the present invention based on the common knowledge of those skilled in the art by using a dimer-forming probe etc.

The capture probe of the present invention and the polymer of the self-aggregated first and second oligonucleotide (signal probe polymer) are preferably separated, and a method of separating the complex is not particularly limited and is preferably a centrifugal separation method or a suction filtration method.

A step of precipitating the capture probe and the complex thereof by the "centrifugation method" is usually performed by centrifugation at 500 to 3000×g for 0.2 to 5 minutes at 20 to 30° C., or centrifugation at 800 to 1500×g for 0.5 to 2 minutes at 23 to 28° C., preferably centrifugation at 1000×g for 1 minute at 25° C. More specifically, the step may be performed in accordance with an instruction manual from a bead manufacturer.

A step of separating the capture probe and the complex thereof by the "suction filtration method" can be performed by the method described in Biochem Biophys Res Commun. 2015 Nov. 27; 467(4):1012-8. Specifically, a solution containing the capture probe and the complex thereof is transferred to a filter plate and is usually sucked in a negative pressure range of 1 to 10 in.Hg at 20 to 30° C., or 1 to 10 in.Hg at 23 to 28° C., preferably, 1 to 5 in.Hg at 25° C. The suction time may be a time until removal of the liquid from the filter is visually observed and is, for example, 1 second to 5 minutes, preferably 5 seconds to 1 minute. The pore size of the filter plate is preferably smaller than the diameter of the capture probe and is preferably 1.2 µm or 1.0 µm, for example. Examples of specific members include a filter plate: MultiScreen™ HTS-BV plate (Merck Millipore, product number: MSBVN1250), a manifold: MultiScreen™ HTS Vacuum Manifold (Merck Millipore), and a suction pump: Chemical duty pump (Merck Millipore, catalog number: WP6110060).

(Sample)

The "sample" used in the method of the present invention is a body fluid such as whole blood, serum, plasma, lymph, urine, saliva, tear fluid, sweat, gastric juice, pancreatic juice, bile, pleural fluid, synovial fluid, cerebrospinal fluid, spinal fluid, and bone marrow fluid, or tissue of liver, kidney, lung, heart etc., of a human, monkey, dog, pig, rat, guinea pig, or mouse. Preferably, the sample is whole blood, serum, plasma, or urine of a human. More preferably, the sample is whole blood, serum, plasma, or urine of a human having received administration of a medicinal drug containing the target oligonucleotide.

A "wash buffer" used in the method of the present invention preferably contains 0.01 to 0.05% surfactant, more preferably 0.02% nonionic surfactant such as Tween 20. Preferably, the nonionic surfactant is Tween 20. More preferably, the "wash buffer" contains 1×PBS ((10×PBS (Nippon Gene, product number: 314-90185 diluted 10 times), 137 mM sodium chloride, 8.1 mM disodium hydrogen phosphate, 2.68 mM potassium chloride, 1.47 mM potassium dihydrogen phosphate, pH 7.4±0.2)), and 0.02% Tween 20. Further preferably, the "wash buffer" contains 1×PBS, 0.02% Tween 20, and 1.5 ppm ProClin300. The "wash buffer" may contain 0.01 to 1%, 0.02 to 0.5%, 0.05 to 0.2%, or 0.1% human serum albumin (HSA) or bovine serum albumin (BSA).

Examples of the method of detecting the polymer of the first and second oligonucleotides of the present invention include a turbidimetric method, an agarose electrophoresis method, an absorbance method, a fluorescence measurement method, and a flow cytometry method, and a flow cytometry method is preferable.

The flow cytometry method is performed, for example, at a "step of detecting a first fluorescence emitted by a first fluorescent substance and a second fluorescence emitted by a second fluorescent substance by using a flow cytometric method", and at the "step of detecting a first fluorescence emitted by a first fluorescent substance and a second fluorescence emitted by a second fluorescent substance by using a flow cytometric method", the first fluorescence emitted by the first fluorescent substance and the second fluorescence emitted by the second fluorescent substance are preferably detected at the same time or at the same opportunity. The phrase "detected at the same time or at the same opportunity" means that the first fluorescence and the second fluorescence emitted from the first fluorescent substance and the second fluorescent substance contained in one complex (three-component complex or four-component complex) simultaneously or sequentially excited in a flow channel of a flow cytometer are detected as the fluorescence emitted from the one complex.

More specifically, examples of the first fluorescent substance include a fluorescent substance contained in the solid phase of the capture probe, and examples of the second fluorescent substance include a fluorescent substance preliminarily bound to a substance specifically binding to the labeling substances added to the first and second oligonucleotides. The flow cytometry method can be used for a reaction solution containing these first and second fluorescent substances to detect the first fluorescence emitted by the first fluorescent substance and the second fluorescence emitted by the second fluorescent substance.

In the present invention, a kit for detecting a target oligonucleotide refers to a kit including at least the following elements:

(1) single-strand-specific nuclease;
(2) a capture probe for capturing a target oligonucleotide; and
(3) a pair of probes capable of self-aggregation composed of first and second oligonucleotides.

The kit also includes the first polynucleotide, ligase, poly(A) polymerase, an assist probe, etc. as needed. The elements are as described above.

EXAMPLES

Example 1

1. Materials and Methods
(a) Target Oligonucleotide

For the target oligonucleotide to be measured, GTI-2040 used by Wei et al. was used (see Wei 2006). The sequence of GTI-2040 is 5'-GGCTAAATCGCTCCACCAAG-3' (SEQ ID NO: 1). For models of the metabolite of the target oligonucleotide (also referred to as "similar substance" in this description), 3'N-1, 3'N-2, 5'N-1, Mismatched GTI-2040, and Scrambled GTI-2040 used by Wei et al. were used. The 3'N-1 and 3'N-2 (SEQ ID NOS: 2 and 3) are oligonucleotides in which the 3' end is deleted by 1 or 2 bases; the 5N-1 (SEQ ID NO: 4) is an oligonucleotide in which the 5' end is deleted by one base; Mismatched GTI-2040 (5'-GGCTAAACTCGTCCACCAAG-3') (SEQ ID NO: 5) is an oligonucleotide having four internal mismatches inside; and Scrambled GTI-2040 (5'-ACGCACTCAGCTAGTGACAC-3') (SEQ ID NO: 6) is an oligonucleotide having the same GC content as GTI-2040 with the order of the bases changed. The synthesis of all the oligonucleotides was requested to Nihon Gene Research Laboratories (HPLC purification grade). The models of the target oligonucleotide and the metabolite of the target oligonucleotide are completely PS-modified (phosphorothioate-modified), as in Wei et al.

(b) Nucleic Acid Probe, Capture Probe

An oligonucleotide probe (nucleic acid probe) complementary to GTI-2040 was bound via $NH_2$ modification of the 3' end to MicroPlex™ Microspheres (Region No. 43, product number: LC10043-01) of Luminex; the 5' end was phosphorylated by using T4 Polynucleotide kinase (Thermo Fisher Scientific, product number: EK0032); and a 20-mer poly(T) oligonucleotide was ligated thereto by using T4 DNA ligase (Thermo Fisher Scientific, product number: 15224-025) to prepare the probes. The binding method was implemented in accordance with a manual collection from Luminex (xMAP™ Cookbook, 3rd Edition). Kinase treatment and ligase treatment were performed in accordance with an attached instruction manual. The sequence of the oligonucleotide probe (nucleic acid probe) complementary to GTI-2040 is 5'-CTTGGTGGAGCGATTTAGCC-3' (SEQ ID NO: 7), and the sequence of the poly(T) oligonucleotide is 5'-TTTTTTTTTTTTTTTTTTTT-3' (SEQ ID NO: 8).

The sequences of a pair of probes capable of self-aggregation used in the method of the present invention have the 5' end labeled with biotin and are 5'-(Biotin)-CAACAATCAGGACGATACCGAT-GAAGTTTTTTTTTTTTTTTTTTTT-3' (the base portion is SEQ ID NO: 9; this is referred to as Ccb4530-1-XY-20T-B) and 5'-(Biotin)-GTCCTGATTGTTGCTTCATCGGTAT-CAAAAAAAAAAAAAAAAAAAA-3' (the base portion is SEQ ID NO: 10; this is referred to as Ccb4530-2-XY-20A-B).

(c) Quantification of Target Oligonucleotide by Method of the Present Invention (1) Preparation of Buffer Solution, Diluent, and Reaction Solution "PAP Mix": Reagents included in a commercially available kit (A-Plus™ Poly(A) Polymerase Tailing Kit, CELLSCRIPT, product number: C-PAP5104H) were used to mix 2 μL of 10× reaction buffer (included in the kit; 0.5 M Tris-HCl (pH 8.0), 2.5 M NaCl, and 100 mM $MgCl_2$), 2 μL of 10 mM ATP (included in the kit), 0.5 μL of poly(A) polymerase (included in the kit), and 5.5 μL of Nuclease-Free Water to prepare a total of 10 μL of PAP Mix. A required amount of PAP Mix was prepared depending on the number of samples.

"Oligonucleotide Solution": The models of the target oligonucleotide to be measured and the metabolite thereof were dissolved in TE (10 mM Tris-HCl (pH8.0), 1 mM EDTA (pH8.0)) at the following concentrations to prepare the oligonucleotide solution: 1,000, 500, 250, 125, 62.5, 31.25 pM for GTI-2040; 125 pM for others. A blank sample containing no oligonucleotide was also prepared.

"First Hybridization Reaction Solution": By mixing 0.33 μL (1500 probes/A) of capture probes, 7.7 μL of 5M tetramethylammonium chloride (TMAC), 5.6 μL of 10× supplement, 1.37 μL of Nuclease-Free Water to prepare a total of 15 μL of a first hybridization reaction solution. The composition of the 10× supplement is 500 mM Tris-HCl (pH8.0), 40 mM EDTA (pH8.0), 8% sodium N-lauroyl sarcosinate. A required amount of the first hybridization reaction solution was prepared depending on the number of samples.

"10× S1 Nuclease Buffer": Eight milliliters of 3M sodium acetate solution (pH 5.2, Fujifilm Wako Pure Chemical Corporation, product number: 316-90081), 13.0906 g of sodium chloride (Kanto Chemical, product number: 37144-00), 8 mL of 0.1 M zinc acetate solution (Fujifilm Wako Pure Chemical Corporation, product number: 267-01575) were sufficiently mixed. The mixture was adjusted to pH 4.5 and diluted in a measuring flask to the total volume of 80 mL with Nuclease-Free Water. The mixture was sterilized with a 0.22 μm filter and was frozen (−20° C.) and stored until use.

"S1 Nuclease Buffer-T": Forty milliliters of 10× S1 Nuclease Buffer and 2 mL of 10% Tween 20 solution (Merck Millipore, product number: 655206) were sufficiently mixed. The mixture was adjusted to pH 4.5 and diluted in a measuring flask to the total volume of 400 mL with Nuclease-Free Water. The mixture was sterilized with a 0.22 μm filter and stored at room temperature.

"S1 Nuclease Master Mix": A total of 75 μL of S1 Nuclease Master Mix was prepared by mixing 7.5 μL of 10× S1 Nuclease Buffer (pH 4.5), 0.056 μL of S1 Nuclease (180 U/μL, Takara Bio, product number: 2410A), and 67.44 μL of Nuclease-Free Water. A required amount of S1 Nuclease Master Mix was prepared depending on the number of samples.

"Self-Aggregation Initiation Mix": By adding and mixing 15 μL of 5M TMAC, 8 μL of 10× supplement, 0.05 μL of 20 pmol/μL Ccb4530-2-XY-20A-B, and 26.95 μL of Nuclease-Free Water, Self-Aggregation Initiation Mix was prepared (total 50 μL). A required amount of Self-Aggregation Initiation Mix was prepared depending on the number of samples.

"Self-Aggregation Mix": By adding and mixing 4.5 μL of 5M TMAC, 2.4 μL of 10× supplement, 1.75 μL of 20 pmol/μL Ccb4530-1-XY-20T-B, 1.4 μL, of 20 pmol/μL of Ccb4530-2-XY-20A-B, and 5.0 μL of Nuclease-Free Water, Self-Aggregation Mix was prepared (total 15 μL). A required amount of Self-Aggregation Mix was prepared depending on the number of samples.

"1×PBS-TP": One×PBS-TP was prepared to final concentration of 1×PBS (10×PBS (Nippon Gene, product number: 314-90185) diluted 10-fold), 0.02% Tween 20, 1.5 ppm ProClin300 (Merck, product number: 48912-U).

"SAPE Solution": PhycoLink™ Streptavidin-R-Phycoerythrin (ProZyme, product number: PJ31S) was diluted with 1×PBS-TP to prepare a 5 μg/mL SAPE solution.

(2) Poly(A) Addition Reaction

To a PCR plate, 10 μL of PAP Mix and 10 μL of the oligonucleotide solution were added and mixed (total 20 μL). The reaction solution was kept warm at 37° C. for 15 minutes by using a thermal cycler, then heat-treated at 65° C. for 10 minutes, and kept at 4° C. until the next treatment.

(3) Capturing of poly(A)-Added Oligonucleotide to Capture Probe (Hybridization)

To the oligonucleotide solution after the poly(A) addition reaction, 15 μL of the first hybridization reaction solution was added and mixed (total 35 μL). The mixture was incubated at 50° C. for 13.5 hours and then kept at 4° C. until the next treatment.

(4) Washing Step

After the incubation, 40 µL of Nuclease-Free Water was added, the mixture was centrifuged at 1000×g at 25° C. for 1 minute to precipitate the beads, and the supernatant was removed by decanting. After 75 µL of S1 Nuclease Buffer-T was added, the mixture was centrifuged at 1000×g at 25° C. for 1 minute to precipitate the beads, and the supernatant was removed by decanting.

(5) S1 Nuclease Treatment

To the beads after the washing step, 75 µL of S1 Nuclease Master Mix was added and mixed to resuspend the beads. The beads were incubated at 37° C. for 30 minutes.

(6) Washing Step

After the incubation, the mixture was centrifuged at 1000×g at 25° C. for 1 minute to precipitate the beads, and the supernatant was removed by decanting. After 75 µL of 0.05% Tween 20 was added, the mixture was centrifuged at 1000×g at 25° C. for 1 minute to precipitate the beads, and the supernatant was removed by decanting.

(7) Self-Aggregation Reaction

To the beads after the washing step, 50 µL of Self-Aggregation Initiation Mix was added and mixed to resuspend the beads. The beads were incubated at 50° C. for 3 minutes (single-strand step) and then incubated at 30° C. for 30 minutes, and after the incubation, 15 µL of Self-Aggregation Mix was added to the mixture and mixed (total 65 µL), and the mixture was incubated at 30° C. for 1 hour (self-aggregation reaction).

(8) Washing Step

After the incubation, the mixture was centrifuged at 1000×g at 25° C. for 1 minute to precipitate the beads, and the supernatant was removed by decanting. After adding 75 µL of 1×PBS-TP at room temperature to each well, the mixture was centrifuged again at 1000×g at 25° C. for 1 minute to precipitate the beads, and the supernatant was removed by decanting.

(9) SAPE Treatment

To each well of the PCR plate, 50 µL of SAPE solution was added and mixed. The PCR plate was allowed to stand at 25° C. for 10 minutes under a light-shielded condition, and SAPE was reacted with biotin.

(10) Washing Excessive SAPE

The PCR plate containing the SAPE reaction solution was centrifuged at 1000×g at 25° C. for 1 minute to precipitate the beads, and the supernatant was removed by decanting. After adding 75 µL of 1×PBS-TP to the bead pellet, the mixture was centrifuged again at 1000×g at 25° C. for 1 minute to precipitate the beads, and the supernatant was removed by decanting. This operation of resuspension, centrifugation, and removal of the supernatant was repeated once again. To the bead pellet, 75 µL of 1×PBS-TP was added and mixed to resuspend the beads.

(11) Fluorescence Detection

The PCR plate containing the resuspended beads was set on a flow cytometer (Luminex system, manufactured by Luminex), and fluorescence from the beads and SAPE conjugates was detected by using the flow cytometer.

2. Test Results (a) Result of Quantification of Target Oligonucleotide by the Method of the Present Invention The result of quantification of the target oligonucleotide by the method of the present invention is shown in FIG. 1. A fluorescent signal dependent on the concentration of the target oligonucleotide in the sample was obtained. A correlation coefficient (r) between the concentration of the target oligonucleotide in the sample and the fluorescence signal was 0.9995, which indicates a high correlation.

(b) Evaluation of Specificity of Quantification of Target oligonucleotide by the Method of the Present Invention Table 1 shows cross-reactivity when the models of the metabolite of the target oligonucleotide were quantified by using the method of the present invention. For the models of the metabolite with the 3' or 5' end deleted, the cross-reactivity was suppressed to about 14 to 26%. For the similar substance having four mismatches inside and the similar substance having the same GC content with the order of the bases changed, the cross-reactivity was suppressed to less than 10%.

TABLE 1

| concentration (pM) | object to be measured | cross-reactivity (%) |
|---|---|---|
| 125 | GTI-2040 | 100 |
| | 3'N-1 | 15.1 |
| | 3'N-2 | 13.5 |
| | 5'N-1 | 25.9 |
| | Mismatched GTI-2040 | <10.0 |
| | Scrambled GTI-2040 | <10.0 | cross-reactivity (%) = [similar substance (MFI − BG)]/[GTI-2040 (MFI − BG)] × 100

Example 2

While the poly(A)-added target oligonucleotide was captured by the capture probe in Example 1, it was confirmed in this example that the target oligonucleotide can be captured by the capture probe containing the sequence complementary to the whole of the target oligonucleotide without adding poly(A) to specifically detect the target oligonucleotide. The self-aggregation reaction was performed via an assist probe.

1. Materials and Methods (1) Preparation of Capture Probe

An oligonucleotide probe (nucleic acid probe) complementary to GTI-2040 was bound via $NH_2$ modification of the 3' end to MicroPlex™ Microspheres (Region No. 43, product number: LC10043-01) of Luminex to prepare the probe (referred to as the capture probe). The sequence of the oligonucleotide probe complementary to GTI-2040 is 5'-CTTGGTGGAGCGATTTAGCC-3' (SEQ ID NO: 7).

(2) Capturing of Target Oligonucleotide to Capture Probe (Hybridization)

To 10 µL of a substance to be measured, 20 µL of the first hybridization reaction solution was added to make a total of 30 µL and was reacted at 50° C. for 13.5 hours.

(2-1) Composition of First Hybridization Reaction Solution

The capture probes prepared in (1): 0.25 µL (500 probes), 5M TMAC: 6.6 µL, 10× supplement [500 mM Tris-HCl (pH8.0), 40 mM EDTA (pH8.0), 8% sodium N-lauroyl sarcosinate]: 4.8 µL, Nuclease-Free Water: 8.35 µL.

(2-2) Substance to Be Measured and Similar Substances

The same substance to be measured (target oligonucleotide) as Example 1 and the same similar substances as Example 1 (3'N-1, 3'N-2, Mismatched GTI-2040, Scrambled GTI-2040) and 3'N-3 (oligonucleotide in which the 3' end of GTI-2040 is deleted by 3 bases) were used and were prepared at the following concentrations by using TE (10 mM Tris-HCl (pH8.0), 1 mM EDTA (pH8.0). The GTI-2040 was prepared at 1,000, 125, and 50 pM, and the others were prepared at 125 pM. A blank sample containing no oligonucleotide was also prepared.

(3) Cleavage Step (S1 Nuclease Treatment)

Thirty microliters of the reaction solution after the capturing step was washed once with Nuclease-Free Water and then washed once with S1 Nuclease Buffer-T. Subsequently, 75 µL of S1 Nuclease reaction solution was added to the washed beads to make a total of 75 µL and was reacted at 37° C. for 30 minutes.

(3-1) Composition of S1 Nuclease Buffer-T 30 mM sodium acetate, 280 mM sodium chloride, 1 mM zinc acetate, 0.05% Tween 20, pH4.5

(3-2) Composition of S1 Nuclease Reaction Solution

10× S1 Nuclease Buffer [300 mM sodium acetate, 2800 mM sodium chloride, 10 mM zinc acetate, pH4.5]: 7.5 µL, S1 Nuclease (180 U/µL, Takara Bio, product number: 2410A): 0.056 µL, Nuclease-Free Water: 67.4 µL (4) Detection Complex Formation Auxiliary Step (Assist Probe Hybridization)

After washing 75 µL of the reaction solution after the cleavage step once with 0.05% Tween 20, 50 µL of AP Hybridization reaction solution was added to the washed beads to make a total of 50 µL, heated at 95° C. for 3 minutes (single-strand step), and reacted at 50° C. for 30 minutes.

(4-1) Composition of AP Hybridization reaction solution

5M TMAC: 15 µL, 10× supplement [500 mM Tris-HCl (pH8.0), 40 mM EDTA (pH8.0), 8% sodium N-lauroyl sarcosinate]: 8 µL, 20 pmol/µL Ccb4530-2-ZYZ-8-B: 0.05 µL, Nuclease-Free Water: 26.95 µL The sequence of the assist probe used in the method of the present invention is 5'-(Biotin)-CCACCAAGCACTCCT-TATATCCTTCATCGGTATCCACTCCTTATATC-3' (the base portion is SEQ ID NO: 11; this is referred to as Ccb4530-2-ZYZ-8-B).

(5) Detection Complex Formation Step (Self-Aggregation Reaction/PALSAR reaction)

To 50 µL of the reaction solution after the detection complex formation auxiliary step, 15 µL of PALSAR reaction solution was added to make a total of 65 µL and was reacted at 30° C. for 1 hour.

The sequences of the pair of probes capable of self-aggregation used in the method of the present invention have the 5' end labeled with biotin and are 5'-(Biotin)-CAACAATCAGGACGATACCGATGAAGGA-TATAAGGAGTG-3' (the base part is SEQ ID NO: 12; this is referred to as Ccb4530-1B), and 5'-(Biotin)-GTCCTGAT-TGTTGCTTCATCGGTATCCACTCCTTATATC-3' (the base part is SEQ ID NO: 13; this is referred to as Ccb4530-2B).

(5-1) PALSAR Reaction Solution 4.5 µL, of 5M TMAC, 2.4 µL, of 10× supplement [500 mM Tris-HCl (pH8.0), 40 mM EDTA (pH8.0), 8% sodium N-lauroyl sarcosinate], 1.75 µL, of 20 pmol/µL Ccb4530-1B, 1.4 µL of 20 pmol/µL Ccb4530-2B, 5.0 µL of Nuclease-Free Water (6) Detection Step (Fluorescence Detection)

After the reaction solution after the detection complex formation step was washed once with 1×PBS-TP [1×PBS [137 mM sodium chloride, 8.1 mM disodium phosphate, 2.68 mM potassium chloride, 1.47 mM potassium dihydrogenphosphate], 0.02% Tween 20, 1.5 ppm ProClin 300], 50 µL of a detection reagent [SAPE (manufactured by Prozyme) 5 µg/mL] was added, and the mixture was allowed to stand for 10 minutes under a light-shielded condition at 25° C. and then washed twice with 1×PBS-TP. Subsequently, 75 µL of 1×PBS-TP was added, and the fluorescence from the beads and SAPE conjugates was measured by Luminex System (manufactured by Luminex) to detect the signal of the substance to be measured.

2. Test Results

Table 2 shows cross-reactivity when the target oligonucleotide and the models of the metabolite (similar substance) thereof were quantified by using the method of Example 2. For the models of the metabolite with the 3' end deleted, the cross-reactivity was suppressed to less than 26%. For the similar substance having four mismatches inside and the similar substance having the same GC content with the order of the bases changed, the cross-reactivity was suppressed to about 30 to 40%.

TABLE 2

| concentration (pM) | substance to be measured | cross-reactivity (%) |
|---|---|---|
| 125 | GTI-2040 | 100 |
|  | 3'N-1 | 25.7 |
|  | 3'N-2 | <0.01 |
|  | 3'N-3 | <0.01 |
|  | Mismatched GTI-2040 | 44.4 |
|  | Scrambled GTI-2040 | 31.7 | cross-reactivity (%) = [similar substance (MFI − BG)]/[GTI-2040 (MFI − BG)] × 100

[Example 3] (Addition of Given Bases)

While poly(A) was added to the target oligonucleotide and this was captured by the capture probe in Example 1, it was confirmed in this example that the target oligonucleotide can be detected after given bases are added instead of poly(A).

1. Materials and Methods (1) Preparation of Capture Probe

An oligonucleotide probe (nucleic acid probe) containing a region complementary to GTI-2040 was bound via $NH_2$ modification of the 3' end to MicroPlex™ Microspheres (Region No.: 43, product number: LC10043-01) of Luminex to prepare the probe. The binding method was implemented in accordance with a manual collection from Luminex (xMAP™ Cookbook, 3rd Edition). The sequence of the nucleic acid probe containing a region complementary to GTI-2040 is 5'-TCGCTATTCCTTGGTGGAGCGATT-TAGCC-3' (SEQ ID NO: 14).

(2) Substance to Be Measured

The same substance as Example 1 was used as the substance to be measured (target oligonucleotide) at 0 and 1,000 pM.

(3) Capturing Step

To 10 µL of the substance to be measured, 10 µL of the hybridization reaction solution [6 µL of 5 M TMAC, 3.2 µL of 10× supplement [500 mM Tris-HCl (pH8.0), 40 mM EDTA (pH8.0), 8% sodium N-lauroyl sarcosinate], 0.2 µL of 1 pmol/µL P-AP2-B, 0.5 µL of capture probes (1000 probes), 0.1 µL of Nuclease-Free Water] was added to make a total of 20 µL and was reacted at 50° C. for 1 hour.

(3-1) Sequence of P-AP2-B (Given Bases)

5'-phosphorylated-GAATAGCGA-Biotin-3'

(4) Ligation Step

With Nuclease-Free Water, 20 µL of the reaction solution after the capturing step was washed once. Subsequently, 50 µL of a ligation reaction solution was added to the washed beads to make a total of 50 µL and was reacted at 50° C. for 1 hour.

(4-1) Composition of Ligation Reaction Solution

10×9° N DNA Ligase Reaction Buffer [100 mM Tris-HCl, 6000 µM ATP, 25 mM magnesium chloride, 25 mM dithiothreitol, 1% Triton X-100, pH 7.5]: 5 µL, 9° N DNA Ligase(*) (40 U/µL, New England Biolabs, Product Number: M0238S): 0.25 µL, Nuclease-Free Water: 44.75 µL (*) 9° N DNA Ligase is an enzyme repairing a nick of DNA and catalyzes a phosphodiester bond between the 3' hydroxy end of the target oligonucleotide and the 5' phosphate end of P-AP-B.

(5) Cleavage Step (S1 Nuclease Treatment)

With S1 Nuclease Buffer-T, 50 μL of the reaction solution after the ligation step was washed twice. Subsequently, S1 Nuclease reaction solution was added to make a total volume of 50 μL and was reacted at 37° C. for 30 minutes.

(5-1) Composition of S1 Nuclease Buffer-T 30 mM sodium acetate, 280 mM sodium chloride, 1 mM zinc acetate, 0.05% Tween 20, pH4.5

(5-2) Composition of S1 Nuclease Reaction Solution

10× S1 Nuclease Buffer [300 mM sodium acetate, 2800 mM sodium chloride, 10 mM zinc acetate, pH4.5]: 5 μL, S1 Nuclease (180 U/μL, Takara Bio, product code: 2410A): 0.056 μL, Nuclease-Free Water: 44.94 μL (6) Detection Step (Fluorescence Detection)

After washing the reaction solution after the cleavage step with 1×PBS-TP [1×PBS [137 mM sodium chloride, 8.1 mM disodium phosphate, 2.68 mM potassium chloride, 1.47 mM potassium dihydrogenphosphate], 0.02% Tween 20, 1.5 ppm ProClin300], 50 μL of the detection reagent [SAPE (manufactured by Prozyme) 5 μg/mL] was added, and the mixture was allowed to stand for 10 minutes under a light-shielded condition at 25° C. and then washed twice with 1×PBS-TP. Subsequently, 75 μL of 1×PBS-TP was added, and the fluorescence from the beads and SAPE conjugates was measured by Luminex System (manufactured by Luminex) to detect the signal of the substance to be measured. In this example, a hybridization reaction product between the adduct of the target oligonucleotide/added bases and the capture probe was directly detected without performing the heat denaturation treatment (single-strand step) and the signal amplification by the PALSAR reaction.

2. Test Results

Table 3 shows signals of the models of the target oligonucleotide (MFI, Median Fluorescent Intensity). A numerical value is shown as a value obtained by subtracting a blank value (signal when the target oligonucleotide was not added (0 pM)). A signal increase was confirmed when the target oligonucleotide was added (1,000 pM) as compared to when the target oligonucleotide was not added (0 pM), and the target oligonucleotide was detected when the given bases were added to the target oligonucleotide.

TABLE 3

| target oligonucleotide (pM) | MFI |
|---|---|
| 0 | 0 |
| 1,000 | 66.5 |

INDUSTRIAL APPLICABILITY

By using the method of detecting or quantifying oligonucleotides of the present invention, drug concentration can be measured in animal or human biological samples having received drug administration, in pharmacokinetic/pharmacodynamic (PK/PD) screening tests at the searching stage of drug development, in safety, pharmacological, and pharmacokinetic tests at the non-clinical stage, and at the clinical stage.

The invention claimed is:

1. A method of detecting a target oligonucleotide in a sample, comprising steps of:
   (i) bringing a capture probe for capturing the target oligonucleotide into contact with the sample,
   the capture probe containing
   (A) a nucleic acid probe, and
   (B) a solid phase, or an adapter or a linker, adjacent to a nucleotide at the 3' end or 5' end of the nucleic acid probe,
   the nucleic acid probe containing a sequence complementary to a complete or partial sequence of the target oligonucleotide;
   (ii) bringing a single-strand-specific nuclease into contact with the sample subjected to the contact step with the capture probe;
   (iii) making the capture probe in the sample single-stranded after the contact step with the single-strand-specific nuclease is performed;
   (iv) bringing a pair of probes capable of self-aggregation composed of first and second oligonucleotides into contact with the sample subjected to the step of making the capture probe single-stranded to form a complex of the capture probe and an oligonucleotide polymer generated by self-aggregation of the first and second oligonucleotides; and
   (v) detecting the complex, and thereby detecting the target oligonucleotide in the sample.

2. The method of detecting a target oligonucleotide according to claim 1, wherein at least one oligonucleotide of the pair of probes capable of self-aggregation composed of the first and second oligonucleotides contains the complete or partial sequence of the target oligonucleotide.

3. The method of detecting a target oligonucleotide according to claim 1, wherein
   the complex forming step of (iv) includes
   a step of bringing into contact with an assist probe containing both the complete or partial sequence of the target oligonucleotide and a sequence complementary to a complete or partial sequence of at least one of the first and second oligonucleotides.

4. A method of detecting a target oligonucleotide in a sample, comprising steps of:

(i) adding the first polynucleotide to the target oligonucleotide in the sample;
(ii) bringing a capture probe for capturing the target oligonucleotide into contact with the target oligonucleotide,
the capture probe containing
(A) a nucleic acid probe,
(B) a solid phase, or an adapter or a linker, adjacent to a nucleotide at the 3' end or 5' end of the nucleic acid probe,
the nucleic acid probe containing a sequence complementary to a complete or partial sequence of the target oligonucleotide and/or a complete or partial sequence of the first polynucleotide;
(iii) bringing a single-strand-specific nuclease into contact with the sample subjected to the step of adding the first polynucleotide and the contact step with the capture probe;
(iv) making the capture probe in the sample single-stranded after the contact step with the single-strand-specific nuclease is performed;
(v) bringing a pair of probes capable of self-aggregation composed of first and second oligonucleotides into contact with the sample subjected to the step of making the capture probe single-stranded to form a complex of the capture probe and an oligonucleotide polymer generated by self-aggregation of the first and second oligonucleotides; and
(vi) detecting the complex, and thereby detecting the target oligonucleotide in the sample.

5. The method of detecting a target oligonucleotide according to claim 4, wherein
(i) the step of adding the first polynucleotide to the target oligonucleotide in the sample is a step of adding the first polynucleotide to the target oligonucleotide in the sample before the contact step with the capture probe.

6. The method of detecting a target oligonucleotide according to claim 4, wherein
(i) the step of adding the first polynucleotide to the target oligonucleotide in the sample is a step of adding the first polynucleotide to the target oligonucleotide in the sample after the contact step with the capture probe.

7. The method of detecting a target oligonucleotide according to claim 4, wherein
at least one oligonucleotide of the pair of probes capable of self-aggregation composed of the first and second oligonucleotides contains the complete or partial sequence of the first polynucleotide.

8. The method of detecting a target oligonucleotide according to claim 4, wherein
the step of forming a complex of (v) includes a step of bringing into contact with an assist probe, and wherein
the assist probe contains the complete or partial sequence of the target oligonucleotide and/or the complete or partial sequence of the first polynucleotide, and a sequence complementary to a complete or partial sequence of at least one of the first and second oligonucleotides.

9. The method of detecting a target oligonucleotide according to claim 4, wherein the first polynucleotide has a poly(A) sequence, a poly(T) sequence, a poly(U) sequence, a poly(T/U) sequence, a poly(G) sequence, or a poly(C) sequence.

10. The method of detecting a target oligonucleotide according to claim 9, wherein the first polynucleotide has a poly(A) sequence.

11. The method of detecting a target oligonucleotide according to claim 1, wherein the first oligonucleotide is an oligonucleotide containing at least a nucleic acid region X, a nucleic acid region Y, and a nucleic acid region Z in order from the 5'-end side, while the second oligonucleotide is an oligonucleotide containing at least a nucleic acid region X' complementary to the nucleic acid region X, a nucleic acid region Y' complementary to the nucleic acid region Y, and a nucleic acid region Z' complementary to the nucleic acid region Z in order from the 5'-end side.

12. The method of detecting a target oligonucleotide according to claim 11, wherein the nucleic acid region Z contains a poly(A) sequence, and wherein the nucleic acid region Z' contains a poly(T) sequence.

13. The method of detecting a target oligonucleotide according to claim 1, wherein the single-strand-specific nuclease is an endonuclease.

* * * * *